United States Patent
Ahmad et al.

(10) Patent No.: US 9,848,075 B1
(45) Date of Patent: Dec. 19, 2017

(54) COMMUNICATION SYSTEM FOR PAIRING USER DEVICES WITH MEDICAL DEVICES

(71) Applicant: Invoy Technologies, LLC, Aliso Viejo, CA (US)

(72) Inventors: Salman Ahmad, Chandler, AZ (US); Zachary Smith, Phoenix, AZ (US); Lubna Ahmad, Chandler, AZ (US)

(73) Assignee: Invoy Technologies, LLC, Aliso Viejo, CA (US)

(*) Notice: Subject to any disclaimer, the term of this patent is extended or adjusted under 35 U.S.C. 154(b) by 0 days.

(21) Appl. No.: 15/156,109

(22) Filed: May 16, 2016

Related U.S. Application Data

(60) Provisional application No. 62/161,753, filed on May 14, 2015.

(51) Int. Cl.
*H04M 1/725* (2006.01)
*H04W 76/02* (2009.01)
(Continued)

(52) U.S. Cl.
CPC ....... *H04M 1/72527* (2013.01); *A61B 5/0022* (2013.01); *A61B 5/024* (2013.01);
(Continued)

(58) Field of Classification Search
CPC ..... G01C 21/26; G01C 21/3469; H04L 67/12; H04L 67/2814; H04W 4/046;
(Continued)

(56) References Cited

U.S. PATENT DOCUMENTS

| 4,147,514 A | 4/1979 | Magers et al. |
| 4,844,867 A | 7/1989 | Bather |

(Continued)

FOREIGN PATENT DOCUMENTS

| EP | 1 524 522 | 4/2005 |
| WO | WO 03/039367 | 5/2003 |

(Continued)

OTHER PUBLICATIONS

U.S. Appl. No. 13/052,963, filed Mar. 21, 2011, Ahmad et al.
(Continued)

*Primary Examiner* — Ankur Jain
*Assistant Examiner* — Max Mathew
(74) *Attorney, Agent, or Firm* — Knobbe, Martens, Olson & Bear, LLP

(57) ABSTRACT

A user device and a breath analysis device (or other types of portable devices) use a pairing and communication protocol that address user convenience and connectivity issues. For example, a breath analysis device is associated with a unique identifier and the unique identifier is associated with an account corresponding to the user. Likewise, a user device is associated with a user device identifier and the user device identifier is associated with the account corresponding to the user. The breath analysis device and the user device can use at least one of the identifiers to determine whether the user device is authorized to pair with the breath analysis device, and vice-versa. If authorized, the breath analysis device and user device can pair with one another. Once paired, the user device may wirelessly communicate with the breath analysis device for various purposes, such as to retrieve and display breath analysis test results.

19 Claims, 15 Drawing Sheets

(51) Int. Cl.
*H04W 4/00* (2009.01)
*H04W 12/06* (2009.01)
*H04W 8/00* (2009.01)
*A61B 5/08* (2006.01)
*A61B 5/00* (2006.01)
*A61B 5/024* (2006.01)

(52) U.S. Cl.
CPC ............ *A61B 5/082* (2013.01); *A61B 5/4806* (2013.01); *A61B 5/681* (2013.01); *H04W 4/001* (2013.01); *H04W 4/008* (2013.01); *H04W 8/005* (2013.01); *H04W 12/06* (2013.01); *H04W 76/021* (2013.01); *H04W 76/023* (2013.01); *A61B 2562/08* (2013.01)

(58) Field of Classification Search
CPC ............... B60K 28/063; B60K 28/066; B60W 2050/143; B60W 2550/402
USPC ................................................. 455/41.1, 41.2
See application file for complete search history.

(56) References Cited

U.S. PATENT DOCUMENTS

| | | | |
|---|---|---|---|
| 4,931,404 A | 6/1990 | Kundu | |
| 4,970,172 A | 11/1990 | Kundu | |
| 5,071,769 A | 12/1991 | Kundu et al. | |
| 5,174,959 A | 12/1992 | Kundu et al. | |
| 5,465,728 A | 11/1995 | Phillips | |
| 5,834,626 A | 11/1998 | De Castro et al. | |
| 6,010,459 A | 1/2000 | Silkoff et al. | |
| 6,067,989 A | 5/2000 | Katzman | |
| 6,190,858 B1 | 2/2001 | Persaud | |
| 6,206,837 B1 | 3/2001 | Brugnoli | |
| 6,221,026 B1 | 4/2001 | Phillips | |
| 6,234,006 B1 | 5/2001 | Sunshine et al. | |
| 6,254,547 B1 | 7/2001 | Phillips | |
| 6,454,723 B1 | 9/2002 | Montagnino | |
| 6,540,691 B1 | 4/2003 | Phillips | |
| 6,582,376 B2 | 6/2003 | Baghdassarian | |
| 6,599,253 B1 | 7/2003 | Baum et al. | |
| 6,607,387 B2 | 8/2003 | Mault | |
| 6,629,934 B2 | 10/2003 | Mault et al. | |
| 6,658,915 B2 | 12/2003 | Sunshine et al. | |
| 6,726,637 B2 | 4/2004 | Phillips | |
| 6,841,391 B2 | 1/2005 | Lewis et al. | |
| 6,981,947 B2 | 1/2006 | Melker | |
| 7,052,854 B2 | 5/2006 | Melker et al. | |
| 7,104,963 B2 | 9/2006 | Melker et al. | |
| 7,220,387 B2 | 5/2007 | Flaherty et al. | |
| 7,300,408 B2 | 11/2007 | Hancock et al. | |
| 7,364,551 B2 | 4/2008 | Allen et al. | |
| 7,373,820 B1 | 5/2008 | James | |
| 7,488,294 B2 * | 2/2009 | Torch .................. | A61B 3/0066 600/372 |
| 7,533,558 B2 | 5/2009 | Flaherty et al. | |
| 7,794,994 B2 | 9/2010 | Cranley et al. | |
| 7,837,936 B1 | 11/2010 | Martin | |
| 7,920,998 B2 | 4/2011 | Brown | |
| 7,976,467 B2 | 7/2011 | Young et al. | |
| 8,021,308 B2 | 9/2011 | Carlson et al. | |
| 8,036,708 B2 | 10/2011 | Oozeki | |
| 8,286,088 B2 | 10/2012 | Shaffer et al. | |
| 8,287,454 B2 | 10/2012 | Wolpert et al. | |
| 8,342,178 B2 | 1/2013 | Hengstenberg et al. | |
| 8,399,837 B2 | 3/2013 | Robbins et al. | |
| 8,514,086 B2 | 8/2013 | Harper et al. | |
| 8,644,760 B2 | 2/2014 | Tuikka | |
| 8,680,974 B2 | 3/2014 | Meiertoberens et al. | |
| 8,816,862 B2 | 8/2014 | Harper et al. | |
| 8,848,189 B2 | 9/2014 | Atkin et al. | |
| 8,871,521 B2 | 10/2014 | Akers | |
| 8,917,184 B2 | 12/2014 | Smith et al. | |
| 9,170,225 B2 | 10/2015 | Dutta et al. | |
| 9,173,595 B2 | 11/2015 | Böhm et al. | |
| 9,299,238 B1 * | 3/2016 | Ahmad ................ | A61B 5/4833 |
| 9,410,712 B2 * | 8/2016 | Smith .................. | H04L 67/141 |
| 9,630,009 B2 * | 4/2017 | Smith ................ | A61N 1/36032 |
| 2002/0084130 A1 * | 7/2002 | Der Ghazarian .... | B60K 28/063 180/272 |
| 2003/0208133 A1 | 11/2003 | Mault | |
| 2004/0018114 A1 | 1/2004 | Wang et al. | |
| 2006/0265018 A1 * | 11/2006 | Smith .................. | A61N 1/372 607/14 |
| 2007/0245810 A1 | 10/2007 | Carter et al. | |
| 2007/0258894 A1 | 11/2007 | Melker et al. | |
| 2008/0008666 A1 | 1/2008 | Phillips | |
| 2008/0053194 A1 | 3/2008 | Ahmad | |
| 2008/0234553 A1 | 9/2008 | Urman et al. | |
| 2009/0054799 A1 | 2/2009 | Vrtis et al. | |
| 2010/0301197 A1 | 12/2010 | Boyle | |
| 2011/0028091 A1 | 2/2011 | Higgins et al. | |
| 2011/0077548 A1 * | 3/2011 | Torch .................... | A61B 3/112 600/558 |
| 2011/0098590 A1 | 4/2011 | Garbutt et al. | |
| 2012/0071737 A1 | 3/2012 | Landini et al. | |
| 2012/0295595 A1 | 11/2012 | Gibori et al. | |
| 2013/0060098 A1 * | 3/2013 | Thomsen .......... | A61B 5/02028 600/301 |
| 2013/0154917 A1 | 6/2013 | Adermann et al. | |
| 2013/0231711 A1 | 9/2013 | Kaib | |
| 2013/0253358 A1 | 9/2013 | Phillips | |
| 2014/0194793 A1 * | 7/2014 | Nakata .................. | A61H 21/00 601/48 |
| 2014/0235171 A1 | 8/2014 | Molettiere et al. | |
| 2014/0276100 A1 | 9/2014 | Satterfield et al. | |
| 2014/0366610 A1 | 12/2014 | Rodriguez | |
| 2015/0073233 A1 | 3/2015 | Rich et al. | |
| 2015/0141073 A1 * | 5/2015 | Shen .................... | G01N 33/497 455/556.1 |
| 2015/0168307 A1 | 6/2015 | Kück et al. | |
| 2015/0289782 A1 | 10/2015 | Peverall et al. | |
| 2016/0146779 A1 | 5/2016 | Gallagher et al. | |
| 2016/0150995 A1 | 6/2016 | Ratto et al. | |
| 2016/0331272 A1 * | 11/2016 | Ahmad ................ | A61B 5/082 |
| 2016/0345910 A1 * | 12/2016 | Ahmad ................ | A61B 5/082 |
| 2017/0119279 A1 * | 5/2017 | Ahmad ................ | A61B 5/097 |
| 2017/0119280 A1 * | 5/2017 | Ahmad ................ | A61B 5/097 |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2014/158365 | 10/2014 |
| WO | WO 2015/134390 | 9/2015 |

OTHER PUBLICATIONS

Ahmad, L. et al., "Design of a Breath Ketone Sensor for Obesity Management", Poster Presentation, Fall meeting of the Biomedical Engineering Society, 2004, in 3 pages.

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O. et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-us.pdf.

(56) References Cited

OTHER PUBLICATIONS

DrägerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en.pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

Ketonix US, "Ketonix 2015 Blue Specifications", 2015, in 2 pages. URL:https://www.ketonix.com/index.php/product-2/ketonix-2015-blue.

Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemistry, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

Landini, B. et al., "Breath Acetone Concentration Measured Using a Palm-Size Enzymatic Sensor System", IEEE Sensors Journal, vol. 9, Dec. 2009, in 6 pages.

Landini, B. et al., "Effect of Exhalation Variables on the Current Response of an Enzymatic Breath Acetone Sensing Device", IEEE Sensors Journal, vol. 10, Jan. 2010, in 6 pages.

Likhodii, S., et al., "Breath Acetone as a Measure of Systemic Ketosis Assessed in a Rat Model of the Ketogenic Diet", Clinical Chemistry, vol. 48 (2002), in 6 pages.

Loken, S. C., "Breath Acetone and Ketone Metabolism in Obese and Diabetic Mice", Diabetes, vol. 25 (1976), in 1 page.

"Figaro Gas Sensor TGS 822", Figaro Engineering Inc., Mar. 1987, in 10 pages.

"MiniMed 530G System User Guide", Medtronic MiniMed, Inc., 2012, in 312 pages.

Musa-Veloso, K. et al., "Breath acetone is a reliable indicator of ketosis in adults consuming keogenic meals", The American Journal of Clinical Nutrition, vol. 76 (2002), in 6 pages.

Schwarz, K., et al., "Breath acetone—aspects of normal physiology related to age and gender as determined in PTR-MS study", Journal of Breath Research, vol. 3 (2009), in 9 pages.

Wang, L. et al., "Nanosensor Device for Breath Acetone Detection", Sensor Letters, vol. 8 (2010), in 4 pages.

Wang, L., "Tailored synthesis and characterization of selective metabolite-detecting nanoprobes for handheld breath analysis", Dissertation Ph. D. Thesis, Stony Brook University, Dec. 2008, in 127 pages.

Yoon, S. et al., "Active control of the depletion boundary layers in microfluidic electrochemical reactors", Lab on a Chip, vol. 6 (2006), in 9 pages.

\* cited by examiner

Fig. 4

COMMUNICATION SYSTEM FOR PAIRING USER DEVICES WITH MEDICAL DEVICES

CROSS-REFERENCE TO RELATED APPLICATIONS

This application claims priority under 35 U.S.C. §119(e) to U.S. Provisional Patent Application No. 62/161,753, entitled "USER AND BREATH ANALYSIS DEVICE PAIRING AND COMMUNICATION" and filed on May 14, 2015, the disclosure of which is hereby incorporated herein by reference in its entirety.

BACKGROUND

The benefits of devices that measure chemical components (e.g., "analytes") in breath are known. Historically, the breath measurements have been captured using relatively large and expensive laboratory equipment in a controlled lab or clinical setting. For example, gas analysis tools, such as selected ion flow tube mass spectroscopy (SIFT-MS) and gas chromatography and mass spectroscopy (GC-MS), require large capital expenditures and trained technicians to operate effectively.

Innovation in the field has been tempered given that individuals skilled in the art typically come from backgrounds of bioinstrumentation, chemistry, and/or physiology. Federal regulations further restrict the types of improvements that can be developed. Thus, it may be difficult to measure chemical components in the breath outside of the lab or clinical setting using existing commercially-viable systems.

SUMMARY

One aspect of the disclosure provides a breath analysis system comprising a portable breath analysis device that includes a wireless transceiver, the portable breath analysis device having a unique identifier; a mobile application configured to run on a mobile device of a user and to communicate wirelessly with the portable breath analysis device; and a server system that stores data that associates the unique identifier of the portable breath analysis system with authentication information of the user. The portable breath analysis device, the mobile application, and the server system are configured to collectively implement a wireless pairing process that creates a wireless protocol pairing between the portable breath analysis device and the mobile device.

The breath analysis system of the preceding paragraph can have any sub-combination of the following features: where the mobile application is configured to initiate the wireless pairing process in response to an input received from the user on the mobile device; where the mobile device is configured to use the unique identifier, as retrieved over a network from the server system based on the authentication information of the user, to determine that the portable breath analysis device is authorized to be wirelessly paired with the mobile device; where the mobile device is further configured to authenticate the portable breath analysis device; where the portable breath analysis device is further configured to authenticate the mobile device; where the portable breath analysis device is configured to initiate the wireless pairing process; where the portable breath analysis device is further configured to authenticate the mobile device; where the mobile device is further configured to authenticate the portable breath analysis device; where the portable breath analysis device is further configured to communicate with the server system to determine that the portable breath analysis device is authorized to pair with the mobile device; where the portable breath analysis device is further configured to use the mobile device as a proxy to communicate with the server system; where communications between the portable breath analysis device and the server system are encrypted using a key not accessible by the mobile device; where the portable breath analysis device is further configured to use a second mobile device as a proxy to communicate with the server system; where the portable breath analysis device is further configured to communicate with the server system without use of the mobile device; and where the wireless protocol pairing is a Bluetooth pairing.

Another aspect of the disclosure provides a non-transitory computer-readable medium having stored thereon a mobile application configured to run on a mobile device of a user. The mobile application comprises executable program code that directs the mobile device to implement a process, the process comprising receiving a first unique identifier from a server in response to an authentication of user credentials; scanning for portable medical measurement devices; receiving, in response to the scanning, a peripheral identification from a first portable medical measurement device; and determining whether to pair with the first portable medical measurement device based on the received peripheral identification and the received first unique identifier.

The non-transitory computer-readable medium of the preceding paragraph can have any sub-combination of the following features: where the process further comprises determining whether the first portable medical measurement device was recognized at a previous time based on a query of a database using the received peripheral identification, in response to a determination that the first portable medical measurement device was recognized at the previous time, pairing with the first portable medical measurement device at least partly in response to a determination that the first portable medical measurement device is eligible to pair with the mobile device, and in response to a determination that the first portable medical measurement device was not recognized at the previous time, requesting and receiving a second unique identifier from the first portable medical measurement device, comparing the first unique identifier with the second unique identifier, and pairing with the first portable medical measurement device in response to a determination that the first unique identifier and the second unique identifier match; where the process further comprises in response to the determination that the first portable medical measurement device was not recognized at the previous time, storing in the database an indication that the first portable medical measurement device is not eligible to pair with the mobile device in response to a determination that the first unique identifier and the second unique identifier do not match; where the process further comprises in response to the determination that the first portable medical measurement devices was not recognized at the previous time, storing in the database an indication that the first portable medical measurement device is eligible to pair with the mobile device in response to the determination that the first unique identifier and the second unique identifier match; where the process further comprises receiving, in response to the scanning, a second peripheral identification from a second portable medical measurement device; where the process further comprises in response to the determination that the first portable medical measurement devices was not recognized at the previous time, assigning a first device identifier to the first portable medical measurement device and a second device identifier to the second portable medical measurement device, transmitting a first instruction to the first portable medical measurement device to display the first device identifier, transmitting a second instruction to the second portable medical measurement device to display the second device identifier, displaying a request to select the first device identifier or the second device identifier, and pairing with the first portable medical measurement device in response to a determination that the first unique identifier and the second unique identifier match and in response to a selection of the first device identifier; where the first device identifier is at least one of a first color, a first reference number, or a first symbol; where the process further comprises, in response to the determination that the first portable medical measurement devices was not recognized at the previous time, assigning a first frequency to the first portable medical measurement device and a second frequency to the second portable medical measurement device, transmitting a first instruction to the first portable medical measurement device to flash a light at the first frequency, transmitting a second instruction to the second portable medical measurement device to flash a light at the second frequency, displaying a request to select the first frequency or the second frequency, and pairing with the first portable medical measurement device in response to a determination that the first unique identifier and the second unique identifier match and in response to a selection of the first frequency; where the process further comprises, in response to the determination that the first portable medical measurement devices was not recognized at the previous time, assigning a first sound to the first portable medical measurement device and a second sound to the second portable medical measurement device, transmitting a first instruction to the first portable medical measurement device to output the first sound, transmitting a second instruction to the second portable medical measurement device to output the second sound, displaying a request to select the first sound or the second sound, and pairing with the first portable medical measurement device in response to a determination that the first unique identifier and the second unique identifier match and in response to a selection of the first sound; where the process further comprises, in response to the determination that the first portable medical measurement devices was not recognized at the previous time, transmitting a first instruction to the first portable medical measurement device to operate a component at a first time, transmitting a second instruction to the second portable medical measurement device to operate the component at a second time, displaying a request to select the first time or the second time, and pairing with the first portable medical measurement device in response to a determination that the first unique identifier and the second unique identifier match and in response to a selection of the first time; where the component is one of an actuator or a pump; where the process further comprises receiving, in response to the scanning, a second peripheral identification from a second portable medical measurement device, and receiving, in response to the scanning, a third peripheral identification from a third portable medical measurement device; where the process further comprises, in response to the determination that the first portable medical measurement devices was not recognized at the previous time, assigning a first device identifier to the first portable medical measurement device, the first device identifier to the second portable medical measurement device, and a second device identifier to the third portable medical measurement device, transmitting a first instruction to the first portable medical measurement device to display the first device identifier, transmitting a second instruction to the second portable medical measurement device to display the first device identifier, transmitting a third instruction to the third portable medical measurement device to display the second device identifier, displaying a request to select the first device identifier or the second device identifier, and receiving a selection of the first device identifier; where the process further comprises, in response to the determination that the first portable medical measurement devices was not recognized at the previous time, assigning the first device identifier to the first portable medical measurement device and the second device identifier to the second portable medical measurement device, transmitting a fourth instruction to the first portable medical measurement device to display the first device identifier, transmitting a fifth instruction to the second portable medical measurement device to display the second device identifier, displaying a second request to select the first device identifier or the second device identifier, and pairing with the first portable medical measurement device in response to a determination that the first unique identifier and the second unique identifier match and in response to a selection of the first device identifier; where the process further comprises, in response to a determination that the first portable medical measurement device was recognized at the previous time, determining whether the first portable medical measurement device is eligible to pair with the mobile device; where the process further comprises terminating the pairing with the first portable medical measurement device in response to one of a selection of a physical reset button or a selection of a reset option within a user interface; where the process further comprises receiving the user credentials from the user, and pairing with the first portable medical measurement device in response to a determination that the first unique identifier and the second unique identifier match and without any input from the user after the user credentials are received; where the first portable medical measurement device is a breath analysis device; where the peripheral identification comprises a hardware address of a transceiver of the first portable medical measurement device; and where the process further comprises receiving the peripheral identification from the first portable medical measurement device via a wireless network.

Another aspect of the disclosure provides a computer-implemented method for pairing with a first user device. The computer-implemented method comprises scanning for user devices available to communicate with a server system; receiving an indication from a second user device that the second user device is available to communicate with the server system; generating a request to retrieve a user device identifier from the server system, where the request comprises an encrypted data portion such that the data portion is not readable by the second user device; transmitting, to the second user device, the request to retrieve the user device identifier from the server system; receiving a response from the second user device, where the response comprises a second data portion including the user device identifier encrypted by the server system such that the second data portion is not readable by the second user device, and where the user device identifier is associated with the first user device; decrypting the second data portion of the response; and connecting with the first user device based on receipt of the user device identifier, said computer-implemented method performed under control of program instructions executed by a portable breath analysis device.

The computer-implemented method of the preceding paragraph can have any sub-combination of the following features: where the first user device and the second user device are the same user device; and where the first user device and the second user device are different user devices.

Another aspect of the disclosure provides a computer-implemented method for pairing with a first user device. The computer-implemented method comprises transmitting, to a server system, a request to retrieve a user device identifier associated with a portable breath analysis device; receiving a response from the server system, where the response comprises the user device identifier, where the user device identifier is associated with the first user device; and connecting with the first user device based on receipt of the user device identifier, said computer-implemented method performed under control of program instructions executed by the portable breath analysis device.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

FIG. 4 illustrates a user interface depicting a user profile, according to one embodiment.

DETAILED DESCRIPTION OF SPECIFIC EMBODIMENTS

Introduction

Figure 1A:
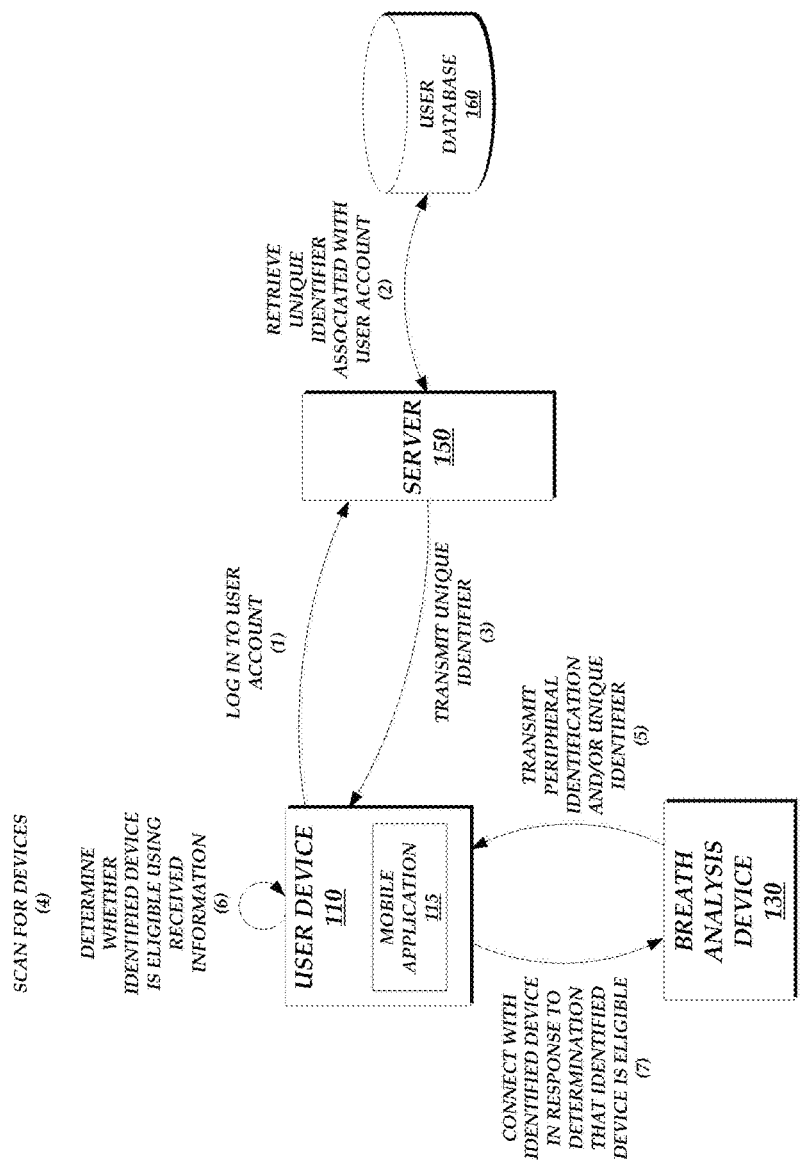
FIG. 1A illustrates a breath analysis device and user device pairing state diagram, according to one embodiment.

As described above, it may be difficult to measure chemical components in the breath outside of the lab or clinical setting using existing commercially-viable systems. Recently, there has been a drive to increase the feasibility and practicality of measuring breath by lowering equipment size, requirements, logistics, costs, and/or the like. Thus, a small, portable, cost-effective breath analysis system is described herein that is suitable for home use and by lay users. The breath analysis system may include a breath analysis device that can integrate with various user devices, such as smartphones, tablets, laptops, and/or the like. The breath analysis device may transmit data that represents a measurable change in an analyte to the user device so that the data can be translated into a user-discernible response and/or forwarded over a network to a server. Examples of breath analysis devices are described in greater detail in U.S. patent application Ser. No. 14/206,347, titled "SYSTEM FOR MEASURING BREATH ANALYTES" and filed on Mar. 12, 2014, and U.S. patent application Ser. No. 13/052,963, titled "SYSTEM FOR ANALYTES IN A FLUID AND RELATED METHOD" and filed on Mar. 21, 2011, the disclosures of which are hereby incorporated herein by reference in their entireties.

However, the integration of the breath analysis device with the user device may pose several challenges. For example, the breath analysis device and the user device (e.g., smartphone) can be paired or linked via a wireless communication protocol, such as Bluetooth or Wi-Fi. These wireless communication protocols, though, typically require users to provide inputs, such as a code or password, that can make the pairing process cumbersome. The wireless communication protocols also do not provide suitable security or authentication features to prevent an unauthorized user from pairing a user device with a breath analysis device.

As another example, a room or network may include multiple breath analysis devices. Such a situation may occur, for example, during a training session to explain to users how to configure and operate the breath analysis device. Existing wireless communication protocols may not be sufficient to allow the user to select the breath analysis device that should be paired with the user's smartphone (or other mobile device) or to determine whether the appropriate breath analysis device is paired with that user device.

Finally, there are some situations in which the breath analysis device and the user device are not in communication with each other when the breath analysis device is ready to transmit the data that represents the measurable change to the user device. Without properly configured communication protocols, data may be lost during the periods in which the two devices are not in communication with each other.

Accordingly, a breath analysis and user device pairing and communication protocol is described herein to address the concerns described above. The breath analysis device or the user device can initiate the pairing of the two devices using the pairing and communication protocol. When the user device initiates the pairing, the user device can also implement a verification process to verify that the breath analysis device is an authorized device (e.g., the user device can authenticate the breath analysis device). Likewise, when the breath analysis device initiates the pairing, the breath analysis device can also implement a verification process to verify that the user device is an authorized device (e.g., the breath analysis device can authenticate the user device). In further embodiments, either the user device or the breath analysis device or both the user device and the breath analysis device can implement a verification process to verify that the other device is an authorized device regardless of which device initiates the pairing.

For example, each breath analysis device may be associated with a unique identifier (e.g., a serial number). When a breath analysis device is acquired by a user, a server may associate the unique identifier with an account corresponding to the user. Before beginning the process of pairing the breath analysis device with a user device (e.g., the user's smartphone), the user may be prompted (e.g., by the server, via instructions received with the breath analysis device, etc.) to install an application on the user device that is configured to communicate with the breath analysis device via the network hardware present on the user device. In an embodiment in which the user device pairs with the breath analysis device, the user device, when executing the application, may prompt the user to log into the user account maintained on the server. Logging into the user account may cause the server to transmit the unique identifier of the breath analysis device to the user device. The user device may then use the unique identifier to identify a breath analysis device that the user is authorized to use and complete the pairing process. Alternatively, in an embodiment in which the breath analysis device pairs with the user device, a breath analysis device can communicate directly with the server or indirectly with the server via any user device running the application. The server may store a user device identifier of the user device and can transmit the user device identifier to the breath analysis device when prompted by the breath analysis device. The breath analysis device can then use the user device identifier to identify a user device associated with the user and complete the pairing process. Verification processes that may be implemented by the breath analysis device and/or the user device during the pairing process are described in greater detail below.

The disclosed pairing and communication protocol may also be used to wirelessly pair a user's mobile device (smartphone) with other types of bodily fluid analysis devices, such as blood analysis devices, urine analysis devices, and/or the like. The disclosed pairing and communication protocol may also be used to wirelessly pair a user's mobile device with other types of portable healthcare or medical devices that are used for health, medical, and/or wellness applications, such as wrist-worn activity monitors, heart rate monitors, pedometers, sleep monitoring devices, and/or the like. For example, such healthcare or medical devices can include devices intended for uses that relate to maintaining or encouraging a general state of health or a healthy activity or that associate the role of a healthy lifestyle with helping to reduce the risk or impact of certain chronic diseases or conditions (e.g., wearable devices for tracking vitals, scales for tracking weight, a breath analysis device, exercise equipment, etc.), where such devices may not be regulated. As another example, such healthcare or medical devices can include instruments, apparatuses, implements, machines, contrivances, implants, in vitro reagents, or other similar articles that are intended for use in the diagnosis of diseases or other conditions; that are intended for use in the cure, mitigation, treatment, or prevention of diseases; or that are intended to affect the structure or any function of the body of humans or other animals, and which does not achieve any of its primary intended purposes through chemical action within or on the body of humans or other animals and which is not dependent upon being metabolized for the achievement of any of its primary intended purposes (e.g., pacemakers, surgical devices, diagnostic devices used for medical purposes, etc.). The term "medical device" is not limited to devices that fall within the definition of the Food, Drug & Cosmetic Act. Rather, the term is intended to be broader, covering portable bodily fluid analysis devices used for other applications, such as weight loss programs, sports or fitness training, and other applications. Thus, the present disclosure is not limited to breath analysis devices. To facilitate an understanding of a particular embodiment and use case scenario, however, the present disclosure will be described primarily in the context of breath analysis devices.

In some embodiments, multiple breath analysis devices are present and the user device receives, from the server, the unique identifiers associated with the multiple breath analysis devices. In such a situation, the user device may assign each of the breath analysis devices a color. The user device may assign each breath analysis device a unique color (e.g., if there are fewer than 7, or some other threshold number of, breath analysis devices present) or may not assign each breath analysis device a unique color (e.g., if there are 7 or more breath analysis devices present). The user device may instruct each breath analysis device to display the assigned color (e.g., via an LED light, a digital or analog display, etc.) such that the color is visible to the user when the user looks at the breath analysis device. The user device may further request the user to select a color that corresponds to the breath analysis device that the user wishes to pair with the user device. If one breath analysis device corresponds with the selected color, then the user device pairs with that breath analysis device. If multiple breath analysis devices correspond with the selected color, then the process may be repeated with only the breath analysis devices that correspond with the selected color until a single breath analysis device corresponds with a selected color.

In an alternate embodiment, the user device may assign a reference number or other symbol to each breath analysis device and instruct the breath analysis device to display the assigned reference number or other symbol. The user device may then request the user to select the appropriate reference number or symbol. In another alternate embodiment, the user device may assign a frequency to each breath analysis device and instruct the breath analysis devices to flash an LED or other light source at the assigned frequency. The breath analysis devices may be instructed to flash the LED or light source at the same time or at different times. The user device may then request the user to select the flashing frequency associated with the desired breath analysis device or to make an indication that a desired breath analysis device is flashing an LED or light source (e.g., if the breath analysis devices are instructed to flash at different times). In another alternate embodiment, the user device may assign a sound to each breath analysis device and instruct the breath analysis devices to make the assigned sound via a noisemaker, vibrator, and/or the like. The breath analysis devices may be instructed to make the sounds at the same time or at different times. The user device may then request the user to select the sound associated with the desired breath analysis device or to make an indication that a desired breath analysis device is making a sound (e.g., if the breath analysis devices are instructed to make sounds at different times). In another alternate embodiment, the user device may instruct each breath analysis device to operate a component (e.g., an actuator, a pump, etc.) at different times. The user device may then request the user to make an indication that a desired breath analysis device has become enabled or is operating the component. The breath analysis and user device pairing process is described in greater detail below with respect to FIGS. 1A through 2B.

The use of the unique identifier to pair the breath analysis and user devices may provide several benefits. For example, the verification of the unique identifier provides an authentication mechanism that removes the need for user input in order to initiate and/or complete the pairing process (e.g., the pairing may occur without any user input, such as entering a passcode, once the user has provided his or her login credentials). In fact, if the user device stores the login credentials for future use such that the user does not have to re-enter the information each time pairing is to take place, then the pairing process may occur without any user action other than an indication to begin the pairing process. As another example, the breath analysis devices may be calibrated on an individual basis. The verification of the unique identifier, in some embodiments, ensures that only the user for which the breath analysis device has been calibrated, uses the breath analysis device to perform tests. The verification of the unique identifier also allows for a controlled number of users to use the same breath analysis device if it is desired that multiple users be able to use the same breath analysis device. As another example, the verification of the unique identifier provides traceability to a specific end user. Traceability may be important because past test results may be calibrated or re-calibrated based on changed circumstances and the use of the unique identifier may allow the server, for example, to identify all test results that need to be modified. Furthermore, traceability to the end user may be important if there are any complaints or malfunctions associated with the breath analysis device and diagnostics are performed.

The user device and the breath analysis device may further use a communication protocol to control the initiation of analyte breath testing and the transmission of data representing the measurable change (e.g., test results). The communication protocol may define the process by which the user device can request or receive test results from the breath analysis device at a time after the testing is complete if, for example, the user device is not in networked communication with the breath analysis device or otherwise is unavailable to receive communications from the breath analysis device when the test results are ready. The communication protocol is described in greater detail below with respect to FIG. 3.

While the disclosure provided below is described with respect to the IEEE 802.15.1 Bluetooth protocol, this is not meant to be limiting. The techniques described herein can be applied to any wireless or wired communications protocol, such as the IEEE 802.11.x protocol, Ethernet, USB, and/or the like.

Breath Analysis and User Device Pairing: State Diagram

Figure 1B:
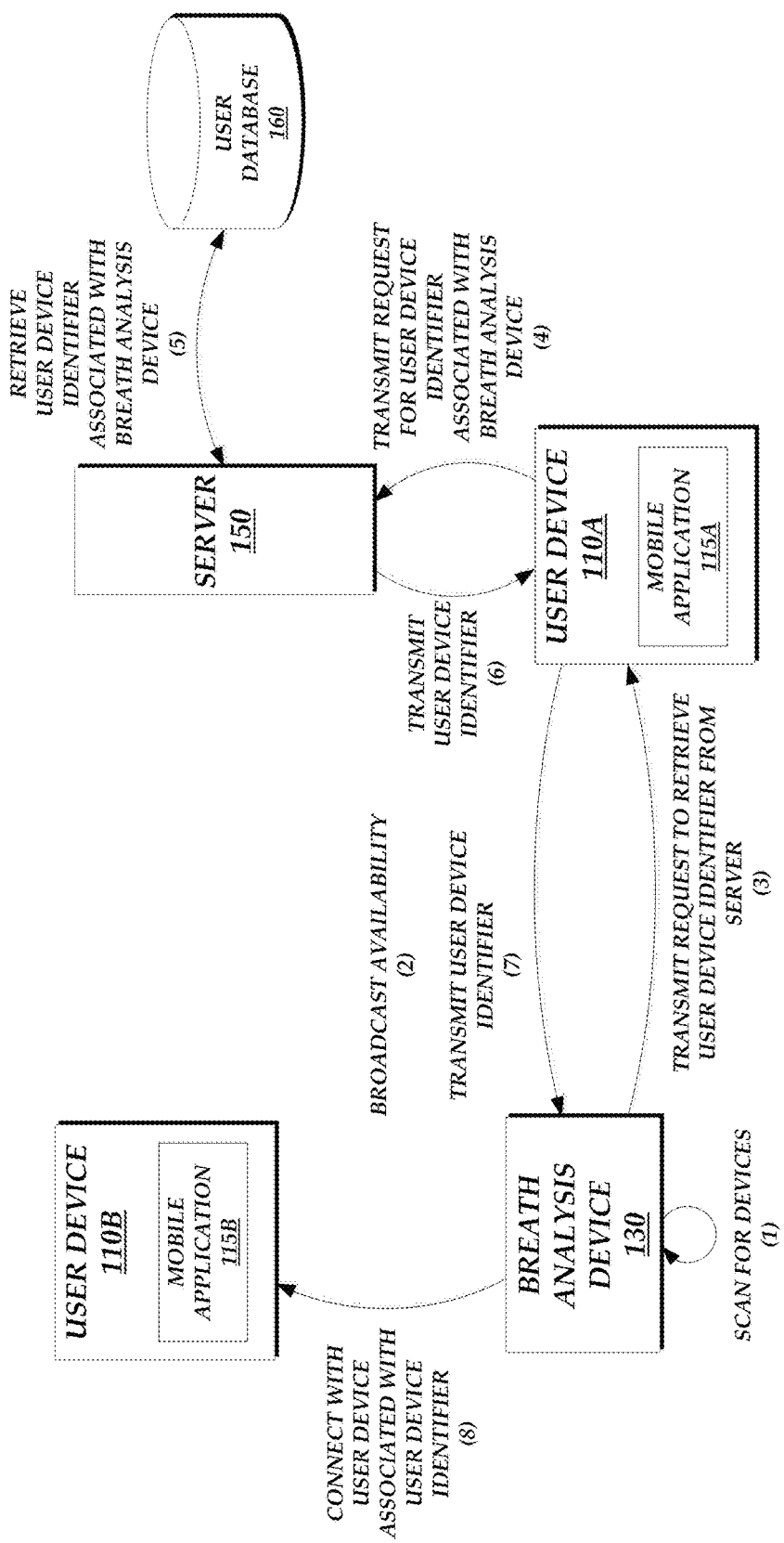
FIG. 1B illustrates another breath analysis device and user device pairing state diagram, according to one embodiment.
Figure 1C:
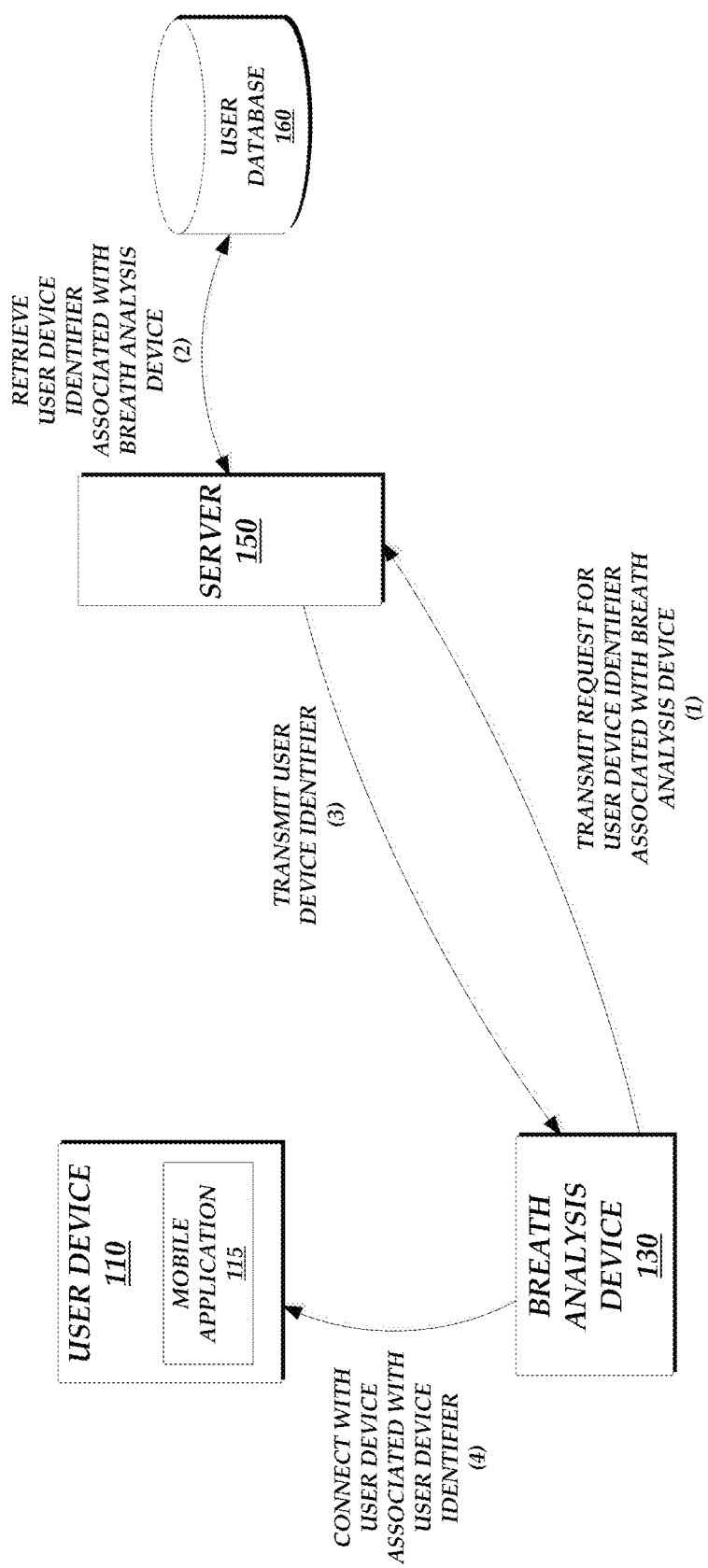
FIG. 1C illustrates another breath analysis device and user device pairing state diagram, according to one embodiment.

FIG. 1A illustrates a breath analysis device 130 and user device 110 pairing state diagram, according to one embodiment. As illustrated in FIG. 1A, the state diagram includes the user device 110, the breath analysis device 130, a server 150, and a user database 160. The user device 110 may further include a mobile application 115. For simplicity, FIG. 1A illustrates a single breath analysis device 130. However, this is not meant to be limiting as any number of breath analysis devices 130 may be present. In a typical use case scenario, the user device 110 shown in FIGS. 1A-1C is a smartphone such as an iPhone or Android-based smartphone, and the pairing is a Bluetooth pairing; however, this need not be the case.

The user device 110 may execute the mobile application 115 to communicate with the breath analysis device 130 and/or the server 150. For example, the mobile application 115 may request the user to enter his or her username and password for a user account managed by the server 150. A user may create the user account when signing up for a diet and/or exercise program and/or when acquiring a breath analysis device 130. Alternatively, the user account may be created by an agent or physician (e.g., via an electronic medical records system). Such credentials may be transmitted to the server 150 so that the user can log in to his or her user account (1).

The server 150 may verify the credentials provided by the user device 110. If the credentials are authenticated, the server 150 may retrieve a unique identifier associated with the user account (2) from the user database 160. The unique identifier may be associated with a single breath analysis device 130. Alternatively, the unique identifier may be associated with a plurality of breath analysis devices 130. For example, the unique identifier may be a wildcard value associated with a plurality of breath analysis devices 130. As another example, the unique identifier may be a set or descriptor of unique identifiers that represent zero or more unique identifiers. The set may be a specific enumeration of unique identifiers, a range of unique identifiers, a regular expression or pattern that matches unique identifiers, and/or the like.

As an example, the user database 160 may store data associated with a user account, such as biographical information, test results, and/or the unique identifiers of any breath analysis devices assigned to the user associated with the user account. Once retrieved, the server 150 may transmit the unique identifier (3) to the user device 110.

In other embodiments, not shown, the user device 110 may not need to receive the unique identifier from the server 150. For example, the mobile application 115 configured to communicate with the breath analysis device 130 may be a custom executable file (or several files within an application package) that is tailored to a specific user. A server that offers the custom executable file (or application package) may either store a cached version of the executable file (or application package) or may dynamically recompile the executable file (or a configuration file within the application package) each time the executable file is requested. In general, a unique identifier may be embedded in the binary of the executable file (or the configuration file) at a specific offset. Whether the server stores the cached version or dynamically recompiles the executable file (or configuration file), when the user requests a copy of the mobile application 115 so that it is installed on the user device 110, the server offering the mobile application 115 may overwrite the bits at the offset such that the executable file (or configuration file) includes a new unique identifier that was not present in the previously downloaded version of the executable file (or configuration file). In some embodiments, the server accesses the account corresponding to the user and the new unique identifier corresponds to the unique identifier associated with the account.

The user device 110 may then begin scanning for breath analysis devices (4). For example, the user device 110 may broadcast a beacon message that is received by any breath analysis device 130 that is within a transmission range of the transceiver of the user device 110. The beacon message may instruct a breath analysis device 130 to transmit a peripheral identification (5) to the user device 110. The peripheral identification may be the hardware address of a transceiver (e.g., a Bluetooth radio transceiver) of the breath analysis device 130. The beacon message (or a subsequent message as described below) may also instruct the breath analysis device 130 to transmit a unique identifier of the breath analysis device 130 (5) to the user device 110.

The user device 110 may use the received information to determine whether the identified breath analysis device 130 is eligible for pairing (6). For example, if the user device 110 determines that the peripheral identification has been received before and that a determination was previously made that the breath analysis device 130 associated with the peripheral identification is eligible for pairing, then the user device connects with the identified breath analysis device 130 (7). If, however, the user device 110 determines that the peripheral identification has been received before and that a determination was previously made that the breath analysis device 130 associated with the peripheral identification is not eligible for pairing, then the user device does not connect with the identified breath analysis device 130.

Furthermore, if the user device 110 determines that the peripheral identification has not been received before, then the user device 110 may request the unique identifier of the breath analysis device 130 (if not already received in response to the beacon message). The user device 110 may compare the unique identifier received from the breath analysis device 130 with the unique identifier received from the server 150. If the comparison yields a match, then the user device 110 may connect with the identified breath analysis device 130 (7). If the comparison does not yield a match, then the user device 110 may not connect with the identified breath analysis device 130.

FIG. 1B illustrates another breath analysis device 130 and user device 110 pairing state diagram, according to one embodiment. As illustrated in FIG. 1B, the state diagram includes user devices 110A and 110B, the breath analysis device 130, the server 150, and the user database 160. Unlike the embodiment disclosed in FIG. 1A, the breath analysis device 130 initiates the connection with a user device 110.

For example, a user device identifier may be associated with a single user device 110 (e.g., a single mobile application 115). The user account of a user can include one or more user device identifiers that identify one or more user devices 110 associated with the user (e.g., one or more user devices 110 that the user uses to access information related to the diet and/or exercise program and/or to run a test using the breath analysis device 130). User device identifiers can thus be stored in the user database 160 in association with a particular user account.

The breath analysis device 130 can use a user device identifier to identify a user device 100 to which to pair. To receive the user device identifier, the breath analysis device 130 can connect directly with the server 150 via a network (see FIG. 1C below) or can connect indirectly with the server 150 via any user device 110 running the mobile application 115. For example, the breath analysis device 130 can connect indirectly with the server 150 if the breath analysis device 130 does not include a transceiver capable of receiving and/or transmitting signals over a network that can access the server 150 (e.g., a Wi-Fi network, a cellular network, etc.). Thus, the breath analysis device 130 can use a user device 110 as a proxy or relay to forward messages between the breath analysis device 130 and the server 150.

In an embodiment, the breath analysis device 130 scans for user devices 110 (1) to serve as a proxy or relay between the breath analysis device 130 and the server 150. The user device 110A can broadcast its availability (2) to serve as the proxy or relay. The user device 110A can begin broadcasting its availability when the mobile application 115A is launched, when a user enables an option in the mobile application 115A to allow the user device 110A to serve as a proxy or relay, when the user device 110A is idle (regardless of whether the mobile application 115A is active or has been launched), and/or when the user device 110A is on (regardless of whether the user device 110A is idle).

The user device 110A can be any user device that is capable of running the mobile application 115A. Furthermore, the user device 110A does not have to be a user device associated with the user of the breath analysis device 130. For example, a first user may wish to use the breath analysis device 130 to run a test. The breath analysis device 130 can use a user device 110A associated with a second user to communicate with the server 150 to retrieve the user device identifier. Thus, the user device used by the breath analysis device 130 to communicate with the server 150 can be different than the user device used by the user to run a test. As another example, the user device used by the breath analysis device 130 to communicate with the server 150 and the user device used by the user to run a test can be the same device.

Once the breath analysis device 130 receives an indication that the user device 110A is available to serve as a proxy or relay, the breath analysis device 130 transmits a request to retrieve a user device identifier from the server 150 (3) to the user device 110A. The request can include authentication information, such as a username and password and/or a unique private access token, such that the server 150 retrieves the correct user device identifier. For example, the user may enter a username and/or password on the breath analysis device 130 using an input device. The breath analysis device 130 can store authentication information such that the user does not have to re-enter the information each time a pairing is to occur or can request the user to re-enter the information before each pairing. Alternatively, each breath analysis device 130 may be provided a unique private access token that is stored in the breath analysis device's 130 memory during manufacturing. The private access token can be randomly generated and/or sufficiently lengthy (e.g., 256 bits) such that it may be practically impossible for an unauthorized user to guess a private access token assigned to any particular breath analysis device 130. While the serial number of the breath analysis device 130 could be used as the private access token, the serial number may serve as a poor private access token because the serial number could be publically available and an unauthorized user may easily guess the number (e.g., serial numbers typically take the form of incrementing integers starting from zero). The private access token of each breath analysis device 130 can be stored in the user database 160 and be associated with an identifier (e.g. a serial number) associated with the breath analysis device 130. The server 150 can then authenticate a request that uses a private access token by ensuring that the received private access token exists in the user database 160 in association with the identifier of the breath analysis device 130. Thus, it may be important that the breath analysis device 130 not transmit or share the device's authentication information with a third party other than the server 150 (e.g., the user device 110A) and/or that any communication by the breath analysis device 130 with the server 150 is encrypted.

In circumstances in which the mobile application 115A is not active or has not been launched and the user device 110A receives a message from the breath analysis device 130, the user device 110A may automatically launch the mobile application 115A to process the message. The mobile application 115A may be launched in the background if the user device 110A is otherwise in use.

Because the user device 110A may not be a user device associated with the user of the breath analysis device 130, the request transmitted by the breath analysis device 130 can be encrypted so that the user device 110A and/or any other third party device cannot read or tamper with the data. For example, the header of a packet transmitted by the breath analysis device 130 that includes the request may include unencrypted information identifying that the source of the packet is a breath analysis device 130. The mobile application 115 may be configured to accept any message that identifies the source as a breath analysis device 130 and forward such message to the server 150. The data portion of the packet can be encrypted by the breath analysis device 130 using public-key cryptography. For example, a public key of the server 150 can be stored in memory of the breath analysis device 130 and be used to encrypt the data portion. The mobile application 115 may not have access to the corresponding private key of the server 150 and thus may not be configured to decrypt the data portion of the packet. Additionally, as long as the mobile application 115 does not have access to the private key of the server 150, the mobile application 115 may be unable to tamper with or change the data portion of the request without the server 150 being able to detect the tampering and thus rejecting the request. Likewise, the response to the request sent from the server 150 to the breath analysis device 130 may be encrypted using the public-key of the breath analysis device 130 such that the mobile application 115 is unable to read or tamper with the data without the breath analysis device 130 being able to detect the tampering.

The encrypted data portion of the request may further include other information including, for example, the serial number of the breath analysis device 130, authentication information (e.g., a private access token or username and password combination), and/or the public-key of the breath analysis device 130 (e.g., for use by the server 150 in encrypting the response to the request transmitted by the breath analysis device 130).

Breath analysis devices 130 may each store a unique public key, share the same public key, and/or rotate through various public keys. Additionally, the breath analysis device 130 may store additional metadata associated with each key, in effect forming a certificate. Metadata found in the certificate can include, for example, the expiration date of the respective key, the issuer of the respective key, the permissions that the respective key grants, a certificate authority, and/or the like.

The server 150 may periodically update its key-pairs. A key-pair comprises a public key (e.g., used to encrypt data) and a corresponding private key (e.g., used to decrypted data). A key-pair may be updated for one of several reasons (e.g., the key-pair has been used a certain number of times, the key-pair is compromised, the key-pair has been used for certain amount of time and expired, etc.). When a key-pair is updated, the new public key of the server 150 may be distributed to the breath analysis device 130. For example, if a public-key is within a threshold time of its expiration date, the breath analysis device 130 may proactively ask the server 150 what the new public-key will be after the expiration date. Alternatively, the server 150 may notice that a breath analysis device 130 is using a soon-to-expire public-key and transmit a new public key to the breath analysis device 130. The exchange of new public keys by the server 150 with the breath analysis device 130 may be completed using encrypted transmissions (e.g., the transmission can be encrypted by the server 150 using the public key that is soon to be updated or an alternate key that is also stored in the breath analysis device 130). Alternatively, a new public key can be stored on the breath analysis device 130 using an input interface, such as a universal serial bus (USB) port (e.g., with the new public key being received from a USB drive).

Using public-key cryptography, the breath analysis device 130 can securely send requests to the server 150 through a user device 110A. When the server 150 receives a request, the server 150 can decrypt the data portion of the request using the private key of the server 150. However, in some embodiments, before processing the request, the server 150 may authenticate the request to ensure that the breath analysis device 130 is actually the entity that the breath analysis device 130 claims to be. For example, the server 150 can authenticate the breath analysis device 130 by using a username and password or a private access token that is included in the request and comparing such information with information stored in the user database 160. The request may also include a public-key associated with the breath analysis device 130. The key-pair to which this public-key belongs may be generated in one of several ways: the breath analysis device 130 may be installed with a specific key-pair or multiple key-pairs during manufacturing, the key-pair may be dynamically generated by the breath analysis device 130 when the breath analysis device 130 is turned on for the first time, and/or the key-pair may be dynamically generated by the breath analysis device 130 before each request to the server 150. When the server 150 transmits a response to the request, the server 150 may encrypt the data portion of the response packet using the public-key associated with the breath analysis device 130 such that only the breath analysis device 130 that sent the original request can decrypt the response using the corresponding private key. In some embodiments, the initial request by the breath analysis device 130 does not include a public-key of the breath analysis device 130. For example, if the key-pair is generated during manufacturing, the private key may be installed on the breath analysis device 130 (e.g., stored in memory of the breath analysis device 130) and the public key may be stored directly in the user database 160 and associated with the private access token. Thus, instead of encrypting data using a public-key included in a request, the server 150 may instead use a public-key stored in user database 160 to encrypt the data included in the response to the request.

The user device 110A can forward the request for the user device identifier associated with the breath analysis device 130 received from the breath analysis device 130 to the server 150 (4). As described above, the request can be included in the data portion of a packet and therefore is encrypted. The server 150 can decrypt the request using a private key associated with the server 150 (e.g., the private key that is in included in the same key-pair as the public key used to encrypt the data). The server 150 can then authenticate the request and/or retrieve the user device identifier associated with the breath analysis device 130 (5) from the user database 160.

The server 150 then transmits the retrieved user device identifier (6) to the user device 110A. The user device identifier can be encrypted in the data portion of the packet such that the user device 110A cannot read the data. The user device 110A then forwards the user device identifier to the breath analysis device 130 (7).

The breath analysis device 130 can decrypt the data portion of the packet that includes the user device identifier and use the user device identifier to find an appropriate user device 110 to pair with. For example, the breath analysis device 130 can broadcast a message to nearby user devices 110 requesting user device identifiers. The message can be broadcast before or after the user device identifier is received from the server 150. The breath analysis device 130 can then connect with the user device 110B associated with the user device identifier received from the server 150 (8). As another example, the user devices 110 running the mobile applications 115 can periodically broadcast their respective user device identifier. Thus, the breath analysis device 130 can receive user device identifiers without prompting the user devices 110 and connect with the user device 110B associated with the user device identifier received from the server 150 (8). As another example, the breath analysis device 130 can transmit a request to connect with the user device 110B associated with the user device identifier received from the server 150 (e.g., the user device identifier can be a MAC address and thus the user device identifier can be set as the destination of the packet) to initiate the connection without knowledge of the user device identifiers of nearby devices. As described above, the user device 110A and the user device 110B can be the same device or different devices.

Once the connection is established, the mobile application 115B can notify the user of the connection. For example, the mobile application 115B can display a color assigned to the connected breath analysis device 130, a serial number or other identifier of the connected breath analysis device 130, a location of the connected breath analysis device 130, etc. and/or can cause the connected breath analysis device 130 to perform an action (e.g., vibrate, make a noise, turn on a light, etc.).

FIG. 1C illustrates another breath analysis device 130 and user device 110 pairing state diagram, according to one embodiment. As illustrated in FIG. 1C, the state diagram includes user device 110, the breath analysis device 130, the server 150, and the user database 160. Similar to the embodiment disclosed in FIG. 1B, the breath analysis device 130 initiates the connection with a user device 110. However, unlike the embodiment disclosed in FIG. 1B, the breath analysis device 130 includes a transceiver capable of communicating with the server 150 over a network.

Because the breath analysis device 130 can communicate directly with the server 150, the breath analysis device 130 transmits a request to the server 150 to retrieve a user device identifier associated with the breath analysis device (1). As described above, the request can include authentication information, such as a username and password or a private access token, such that the server 150 retrieves the correct user device identifier.

As described above, the request can be encrypted by the breath analysis device 130 using the public key of the server 150. The server 150 can decrypt the request using the private key of the server 150 and authenticate the request using the authentication information. The server 150 can then retrieve the user device identifier associated with the breath analysis device 130 (2) from the user database 160.

The server 150 then transmits the retrieved user device identifier (3) to the breath analysis device 130. The breath analysis device 130 can decrypt the data portion of the packet that includes the user device identifier and use the user device identifier to find an appropriate user device 110 to pair with. Once identified, the breath analysis device 130 can connect with the user device 110 associated with the user device identifier. Once the connection is established, the mobile application 115 can notify the user of the connection as described above.

In further embodiments, not shown, the breath analysis device 130 can implement verification procedures to ensure that the connected user device 110 is not spoofing an actual user device 110 operated by the user or is otherwise unauthorized. For example, once the breath analysis device 130 and the user device 110 or 110B are connected, the breath analysis device 130 can prompt the user device 110 or 110B to complete a challenge. This challenge may involve the participation of the user or may be completed automatically by the mobile application 115. Successful completion of the challenge can provide a confirmation that the user device 110 or 110B is authorized to communicate with the breath analysis device 130. The challenge can include the breath analysis device 130 instructing the connected user device 110 or 110B to authenticate with the server 150 and provide proof that the user device 110 or 110B was able to successfully authenticate.

In an embodiment, the challenge involves the breath analysis device 130 generating a new key-pair and encrypting the new public key along with a unique identifier using the public key of the server 150. This encrypted payload can be transmitted by the breath analysis device 130 to the connected user device 110 or 110B. The connected user device 110 or 110B can authenticate with the user using its device identifier and provide the encrypted payload to the server 150. The server 150 can decrypt the encrypted payload using the private key of the server 150 and extract the public key of the breath analysis device 130 from the decrypted payload. The server 150 may then encrypt at least one of the authenticated user device identifier of the user device 110 or 110B or the unique identifier (or peripheral identification) of the breath analysis device 130 the user device 110 or 110B can connect to with the extracted public key and transmit this encrypted payload as a response back to the connected user device 110 or 110B. The connected user device 110 or 110B can forward the response to the breath analysis device 130. The breath analysis device 130 can decrypt the data portion of the response using the private key generated when the breath analysis device 130 initially sent the challenge request (e.g., the private key generated as part of the generated new key-pair). If the peripheral identification or unique identifier included in the response matches the peripheral identification or unique identifier of the breath analysis device 130 and the user device identifier or other user identifier in the response matches the user device identifier or other user identifier previously retrieved by the breath analysis device 130, then the breath analysis device 130 verifies that the packet originated from the server 150 and thus that the user device 110 or 110B is authorized to communicate with the breath analysis device 130. For example, if the user device 110 or 110B is unauthorized and generates the packet itself rather than requesting the packet from the server 150, then the decrypted data of the packet would not match the expected identifiers because the user device 110 or 110B does not have access to the key-pair stored in the breath analysis device 130 and the server 150.

In another embodiment, the challenge can involve a scheme similar to two-factor authentication in which the breath analysis device 130 requests that the server 150 generate two tokens (e.g., a public token and a secret token) and associate the two tokens with a device identifier. The breath analysis device 130 then provides the public token to the connected user device 110 or 110B. The connected user device 110 or 110B requests the secret token from the server 150 by first authenticating with the server 150 and thereby providing its device identifier. The connected user device 110 or 110B then provides the public token to the server 150. The server 150 may only provide the secret token if the connected user device 110 or 110B successfully authenticates and the public token is associated with the device identifier of the user device 110 or 110B. The connected user device 110 or 110B then provides the secret token to the breath analysis device 130. The breath analysis device 130 can confirm whether the secret token received from the connected user device 110 or 110B matches the secret token generated by and provided by the server 150. If the secret tokens match, the breath analysis device 130 determines that the connected user device 110 or 110B was able to authenticate with the server 150 using the broadcasted device identifier of the user device 110 or 110B (e.g., otherwise, the user device 110 or 110B would not have access to the secret token) and thus is authorized to use the breath analysis device 130.

The verification process described above is described in the context of an embodiment in which the breath analysis device 130 initiates pairing with the user device 110 or 110B. In these embodiments, the breath analysis device 130 is verifying the identity of the user device 110 or 110B. However, this verification process may also take place in embodiments such as FIG. 1A in which the user device 110 initiates pairing with the breath analysis device 130 and the user device 110 is verifying the identity of the breath analysis device 130. Moreover, it is also possible that both verification processes take place. For example, the breath analysis device 130 may verify the identity of the user device 110 and the user device 110 may verify the identity of the breath analysis device 130 (e.g., no matter which device initiates the pairing). The verification process performed by the user device 110 may be similar to the verification process described above with the roles of the user device 110 and the breath analysis device 130 reversed.

Breath Analysis and User Device Pairing: Flow Diagrams

Figure 2A:
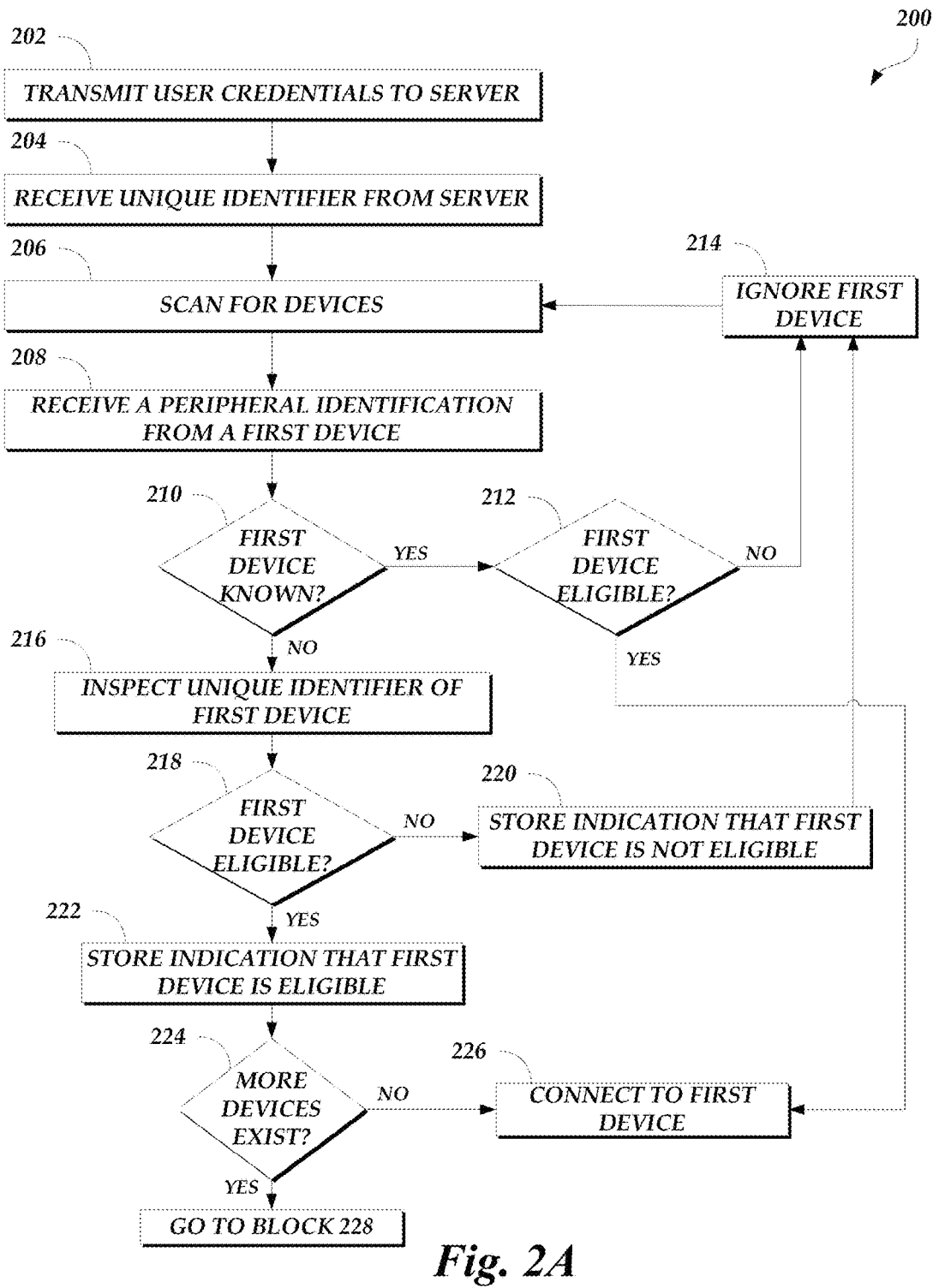
FIGS. 2A-2B illustrate a breath analysis device and user device pairing and selection process that may be implemented at least by the user device, according to one embodiment.
Figure 2B:
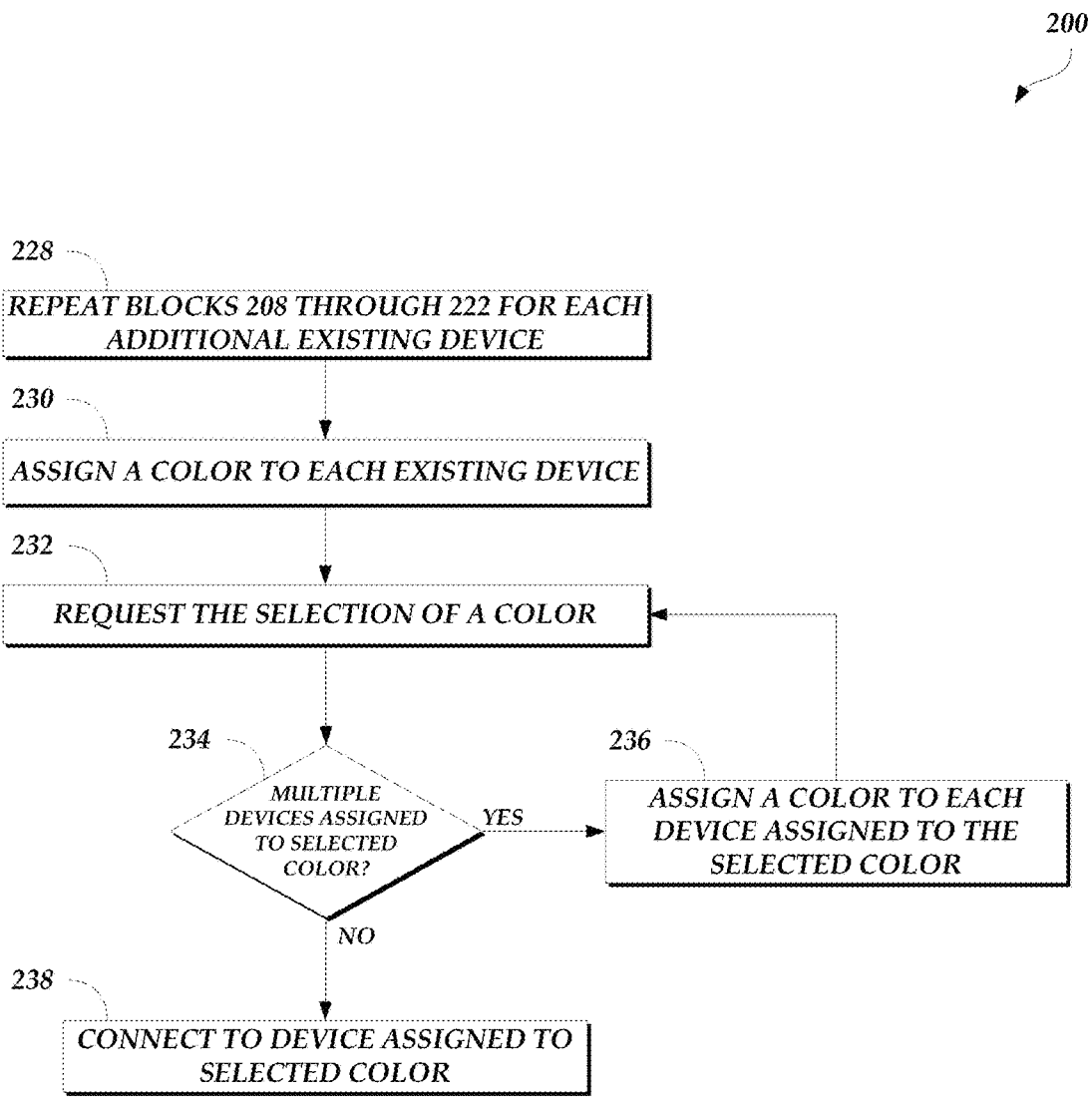

FIGS. 2A-2B illustrate a breath analysis device 130 and user device 110 pairing and selection process 200 that may be implemented at least by the user device 110, according to one embodiment. For example, the application described herein that is configured to communicate with breath analysis devices 130 (e.g., the mobile application 115) may include executable program code that directs the user device 110 to implement the pairing and selection process 200. The pairing and selection process 200 begins at block 202. In an embodiment, all of the steps/blocks illustrated in FIGS. 2A-2B are performed by the user device 110 under control of the executable program instructions of the mobile application 115.

At block 202, user credentials are transmitted to the server, such as the server 150. For example, the user may view a login screen using the mobile application 115 and provide user credentials corresponding to an account associated with the user. The user credentials may include the username and password used to log into an account associated with the user of the user device 110.

At block 204, a unique identifier is received from the server. The unique identifier may be received in response to a successful log in to the account associated with the user of the user device 110. The received unique identifier may be the unique identifier associated with the breath analysis device 130 acquired by the user. In some embodiments, multiple unique identifiers may be received from the server (e.g., if multiple breath analysis devices 130 have been acquired by the user).

At block 206, a scan for breath analysis devices is performed. The scan may involve the transmission by the user device 110 of beacon messages used to solicit responses from breath analysis devices 130 that are in the transmission range of the user device 110.

At block 208, a peripheral identification is received from a first breath analysis device. For example, a solicited response may include the peripheral identification. In an embodiment, the peripheral identification is the hardware address of the transceiver of the first breath analysis device.

At block 210, a determination is made as to whether the first breath analysis device is known. For example, the user device 110 may store, in a local database or volatile or non-volatile memory, a list of peripheral identifications that have been received at previous times. In addition, the user device 110 may store an indication of whether such peripheral identifications are associated with breath analysis devices that are eligible for pairing with the user device 110. If a determination is made that the first breath analysis device is known (e.g., the received peripheral identification was also received at a previous time), then the pairing and selection process 200 proceeds to block 212. Otherwise, the pairing and selection process 200 proceeds to block 216.

At block 212, a determination is made as to whether the first breath analysis device is eligible for pairing with the user device. For example, as described above, in addition to storing the received peripheral identification, the user device 110 may also store an indication of whether breath analysis device associated with the peripheral identification is eligible for pairing (and the process by which this indication is made is described below). The user device 110 may query the local database or memory to determine whether the first breath analysis device is eligible for pairing. If a determination is made that the first breath analysis device is eligible for pairing with the user device 110, then the pairing and selection process 200 proceeds to block 226. Otherwise, the pairing and selection process 200 proceeds to block 214.

At block 214, the first breath analysis device is ignored (e.g., the user device 110 does not connect with the first breath analysis device). The pairing and selection process 200 proceeds back to block 206 to scan for other breath analysis devices 130.

At block 216, the unique identifier of the first breath analysis device is inspected. For example, the user device 110 may request the unique identifier from the first breath analysis device. The first breath analysis device may then transmit its unique identifier to the user device 110.

At block 218, a determination is made as to whether the first breath analysis device is eligible for pairing with the user device. For example, the user device 110 compares the unique identifier received from the server with the unique identifier received from the first breath analysis device. If the unique identifiers match, then the user device 110 may determine that the first breath analysis device is eligible for pairing with the user device and the pairing and selection process 200 proceeds to block 222. Otherwise, if the unique identifiers do not match, then the user device 110 may determine that the first breath analysis device is not eligible for pairing with the user device and the pairing and selection process 200 proceeds to block 220. Whether a unique identifier received from the server matches the unique identifier received from the first breath analysis device may depend on the type of unique identifier received from the server. For example, if the unique identifier is a single unique identifier value, then there may be a match if the unique identifiers are the same set of characters. As another example, if the unique identifier is a wildcard or represents one or more unique identifiers, then there may be a match if the unique identifier received from the first breath analysis device satisfies the wildcard expression, matches one of the enumerated unique identifiers, falls within a range of unique identifiers, matches a regular expression or pattern that matches unique identifiers, and/or the like.

At block 220, an indication that the first breath analysis device is not eligible for pairing is stored. For example, the indication may be stored in the local database or memory in association with the received peripheral identification of the first breath analysis device. This indication may be used, as described in block 212, if the same peripheral identification is received in the future. The pairing and selection process 200 then proceeds back to block 214 to ignore the first breath analysis device and scan for other breath analysis devices 130.

At block 222, an indication that the first breath analysis device is eligible for pairing is stored. As described above, this indication may be used in block 212 if the same peripheral identification is received in the future.

At block 224, a determination is made as to whether more breath analysis devices exist. For example, multiple breath analysis devices 130 may respond to the beacon messages transmitted by the user device 110. If multiple breath analysis devices 130 exist, then the pairing and selection process 200 proceeds to block 228. Otherwise, the pairing and selection process 200 proceeds to block 226.

At block 226, a connection to the first breath analysis device is established. Thus, the pairing and selection process 200 may end, resulting in the pairing of the user device 110 to the first breath analysis device. Such pairing may occur without any user input other than the entering of login credentials.

At block 228, blocks 208 through 222 are repeated for each additional existing breath analysis device. Thus, the pairing and selection process 200 may determine which breath analysis devices 130 are eligible for pairing with the user device 110 and which are not.

At block 230, a color is assigned to each existing breath analysis device 130 that is eligible for pairing with the user device 110. As described above, a different color may be assigned to each existing breath analysis device 130 (e.g., if less than 7 breath analysis devices 130 exist) or the same color may be assigned to multiple breath analysis devices 130 (e.g., if 7 or more breath analysis devices 130 exist). While the color spectrum may include a wide variety of distinct colors, colors may be chosen such that they are easily distinguishable from other chosen colors to avoid user confusion. Thus, if many breath analysis devices 130 exist, colors may be repeated.

At block 232, the selection of a color is requested. For example, the user device 110 may instruct each breath analysis device to display its assigned color (e.g., via an LED, a digital or analog display, etc.). The user device 110 may also prompt the user to determine the displayed color of the breath analysis device 130 that the user wants to pair with the user device 110 and then to select the color.

At block 234, a determination is made as to whether multiple breath analysis devices 130 are assigned to the selected color. If multiple breath analysis devices are assigned to the selected color, then the pairing and selection process proceeds to block 236. Otherwise, the pairing and selection process proceeds to block 238.

At block 236, a color is assigned to each breath analysis device that was previously assigned to the selected color. For example, if the number of existing breath analysis devices 130 is ten and two of the ten existing breath analysis devices 130 were assigned to the selected color of blue, then only those two breath analysis devices 130 may be assigned a new color. The other eight breath analysis devices 130 (e.g., the breath analysis devices 130 assigned to colors other than the selected color of blue) may be instructed to remove the display of any assigned color. The pairing and selection process 200 may then proceed back to block 232 such that the user is prompted to select a color based on colors assigned to the breath analysis devices 130 that were previously assigned a color selected by the user (e.g., the two breath analysis devices 130 previously assigned the color blue).

At block 238, a connection is established to the breath analysis device assigned to the selected color. Thus, the pairing and selection process 200 may perform a recursive process to allow the user to narrow down the number of possible breath analysis devices 130 via color selection until a single breath analysis device 130 is selected for pairing. This recursive process may apply no matter how many breath analysis devices 130 are eligible for pairing with the user device 110.

In an alternative embodiment, as part of the pairing and selection process 200, the user device may assign a reference number or other symbol to each breath analysis device instead of (or in addition to) a color and instruct the breath analysis device to display the assigned reference number or other symbol. The user device may then request the user to select the appropriate reference number or symbol. In another alternate embodiment, the user device may assign a frequency to each breath analysis device instead of (or in addition to) a color and instruct the breath analysis devices to flash an LED or other light source at the assigned frequency. The breath analysis devices may be instructed to flash the LED or light source at the same time or at different times. The user device may then request the user to select the flashing frequency associated with the desired breath analysis device or to make an indication that a desired breath analysis device is flashing an LED or light source (e.g., if the breath analysis devices are instructed to flash at different times). In another alternate embodiment, the user device may assign a sound to each breath analysis device instead of (or in addition to) a color and instruct the breath analysis devices to make the assigned sound via a noisemaker, vibrator, and/or the like. The breath analysis devices may be instructed to make the sounds at the same time or at different times. The user device may then request the user to select the sound associated with the desired breath analysis device or to make an indication that a desired breath analysis device is making a sound (e.g., if the breath analysis devices are instructed to make sounds at different times). In another alternate embodiment, the user device may instruct each breath analysis device to operate a component (e.g., an actuator, a pump, etc.) at different times instead of (or in addition to) assigning each a color. The user device may then request the user to make an indication that a desired breath analysis device has enabled or is operating the component.

In any of the alternate embodiments described above, the pairing and selection process 200 can assign multiple breath analysis devices to have the same reference number, symbol, frequency, and/or sound and/or to operate the same component at the same time and can perform procedures similar to those outlined in blocks 232, 234, and 236 above to ultimately identify a single breath analysis device for pairing.

During any of blocks 202 through 238, the user may reset the pairing and selection process 200. For example, the user may engage a physical button (e.g., on the user device 110) or select a reset option via a user interface (e.g., using the user device 110). Resetting the pairing and selection process 200 may cause the pairing and selection process 200 to revert back to block 202 (e.g., the reset may cause the user to log out of the user account and/or may cause the user device 110 to terminate any pairing with the breath analysis device 130 that may have occurred) or to block 206 (e.g., the reset may not cause the user to log out of the user account and/or may cause the user device 110 to terminate any pairing with the breath analysis device 130 that may have occurred).

Likewise, during any of blocks 202 through 238, the user may perform a partial reset of the pairing and selection process 200 (e.g., to correct a mistake), which may cause the pairing and selection process 200 to revert back to the previous block or several blocks before the current block. For example, the user may have selected the incorrect color in block 232. A physical button (on the user device 110) or a virtual button displayed within a user interface (on the user device 110) may allow the user to cause the pairing and selection process 200 to proceed from block 234 back to block 232 so that the user can make another selection. If the user device 110 pairs with the breath analysis device 130 before the physical or virtual button is selected, selection of the physical or virtual button may cause the user device 110 to terminate the pairing with the breath analysis device 130.

Testing Initiation and Data Retrieval

Figure 3:
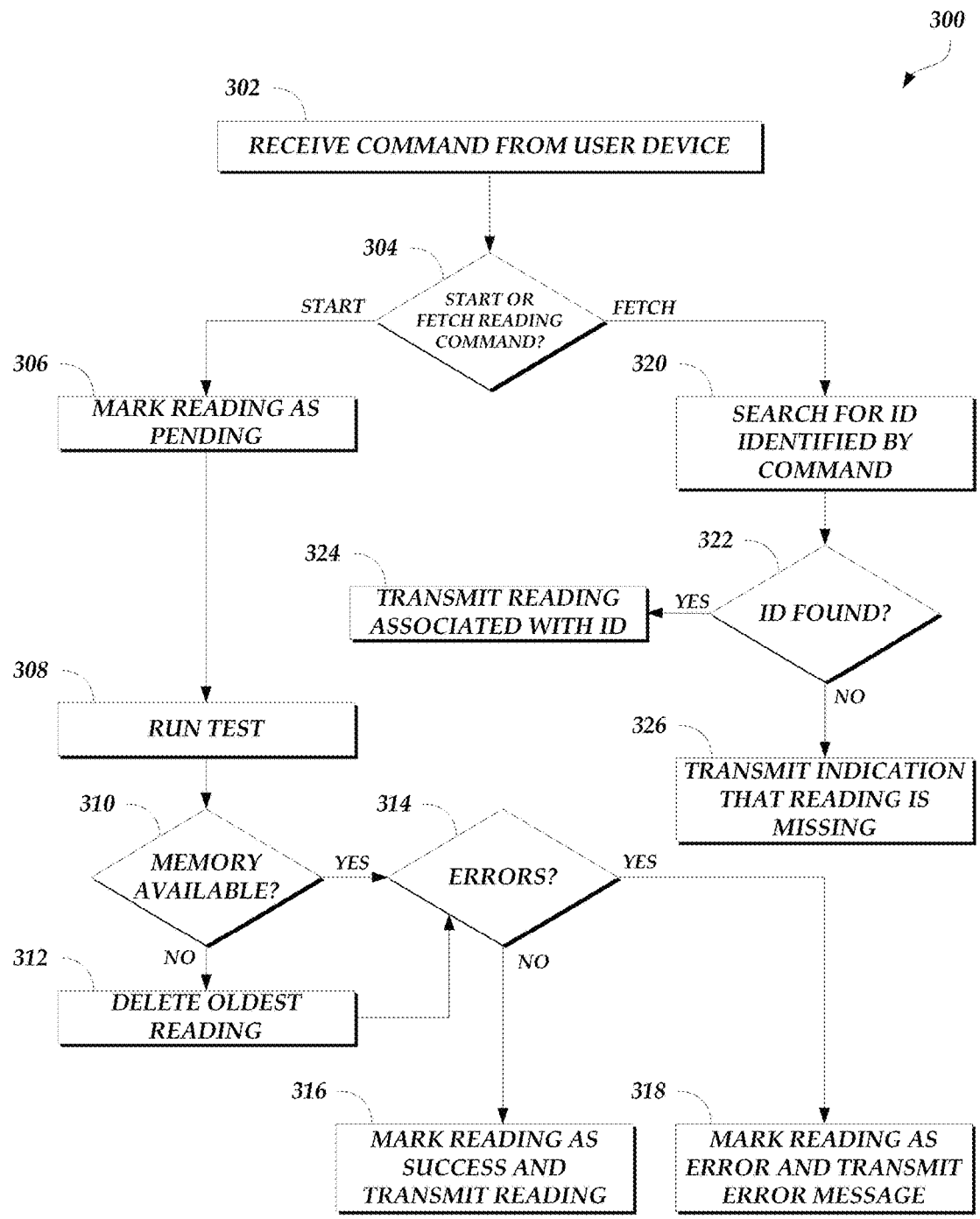
FIG. 3 illustrates a process for measuring and transmitting test results that may be implemented by a breath analysis device, according to one embodiment.

FIG. 3 illustrates a process 300 for measuring and transmitting test results that may be implemented by a breath analysis device, according to one embodiment. For example, the process 300 may be implemented by the breath analysis device 130. Any tasks and functions described below as implemented by the user device 110 may be embodied in, and controlled by, the mobile application 115. The process 300 begins at block 302.

At block 302, a command from a user device is received. For example, the user device 110 may transmit a start reading command or a fetch reading command. The start reading command may be an instruction from the user device 110 to the breath analysis device 130 to start a test. The fetch reading command may be an instruction from the user device 110 to the breath analysis device 130 to transmit results from a test that was already performed. The fetch reading command may be sent if, for example, the user device 110 and the breath analysis device 130 were disconnected when the breath analysis device 130 completed a requested test. The user device 110 may be aware that a test was requested (e.g., via a start reading command), but that no test results were received in response to the requested test. The user device 110 may be so aware because the user device 110 may have generated an identification parameter value (described below), but have no results corresponding to the generated identification parameter value. Thus, at a time that the user device 110 is once again connected to the breath analysis device 130 and/or after a threshold amount of time has expired since the test was requested, the user device 110 may automatically transmit the fetch reading command.

At block 304, the process 300 determines whether a start reading command or a fetch reading command was received. If a start reading command is received, the process 300 proceeds to block 306. (In an embodiment, the user device 110 sends the start reading command in response to the user selecting a virtual or physical "start" button of the mobile application 115.) If a fetch reading command is received, the process 300 proceeds to block 320.

At block 306, a reading is marked as "pending." For example, a reading may be created that includes three parameters: an identification, a value, and a state. The identification parameter may be assigned a value to differentiate this reading from any past or future readings. In an embodiment, the identification parameter value is a large random number (e.g., 32 bit number, 64 bit number, etc.). The identification parameter value may be generated by the breath analysis device 130 or provided by the user device 110 via the start reading command. If the identification parameter value is generated by the breath analysis device 130, the breath analysis device 130 may report the generated identification parameter value to the user device 110 at or near a time that the identification parameter value is generated. The value parameter may store the test results. Initially, the value parameter may be set to zero. The state parameter may indicate a status of the test. Initially, the state parameter may be marked as "pending."

At block 308, a test is run. For example, the test is run by the breath analysis device 130. The running of the test may provide test results, such as a measurable change in an analyte found in a breath sample.

At block 310, the process 300 determines whether there is memory available to store the test results. If a determination is made that there is not enough memory to store the test results, then the process 300 proceeds to block 312. Otherwise, the process 300 proceeds to block 314.

At block 312, an oldest reading is deleted. For example, the oldest reading may be deleted to increase the amount of available memory. Deletion of the oldest reading may include deleting the identification parameter, the value parameter, and/or the state parameter associated with the oldest reading. The process 300 then proceeds to block 314.

At block 314, a determination is made as to whether any errors occurred during the test. If any errors occurred, the process 300 proceeds to block 318. If no errors occurred, the process 300 proceeds to block 316.

At block 316, the reading is marked as "success" and transmitted to the user device 110. For example, the value parameter may be assigned a value corresponding to the test results and the state parameter may be marked as "success." The reading may be stored on the breath analysis device 130 and transmitted to the user device 110. The reading may be stored in case there are communication issues between the user device 110 and the breath analysis device 130.

At block 318, the reading is marked as "error" and transmitted to the user device 110. For example, the state parameter may be marked as "error." In an embodiment, even though the test resulted in one or more errors, the value parameter still may be assigned a value corresponding to the test results (e.g., so users and/or agents are aware of the problematic test results). The reading may be stored on the breath analysis device 130 and transmitted to the user device 110. Once the reading is transmitted to the user device 110 (either during block 316 or block 318), the process 300 ends.

At block 320, a search for the identification parameter value included in the fetch reading command is performed. For example, the fetch reading command may include the identification parameter value of the reading desired by the user device 110. The breath analysis device 130 may search a local database or memory to locate the received identification parameter value.

At block 322, a determination is made as to whether the identification parameter value is found. If the identification parameter value is found, the process 300 proceeds to block 324. Otherwise, the process 300 proceeds to block 326.

At block 324, the reading associated with the received identification parameter value is transmitted to the user device 110. The user device 110 may transmit an acknowledgment if the reading is successfully received. Receipt of the acknowledgment may cause the breath analysis device 130 to delete the reading from memory. Once the reading is transmitted to the user device 110, the process 300 ends.

At block 326, an indication that the reading is missing may be transmitted to the user device 110. For example, a new reading may be generated that includes the identification parameter value received via the fetch reading command, a value parameter of zero, and a state parameter of "missing." Once the generated reading is transmitted to the user device 110, the process 300 ends.

User Interfaces

Figure 4:
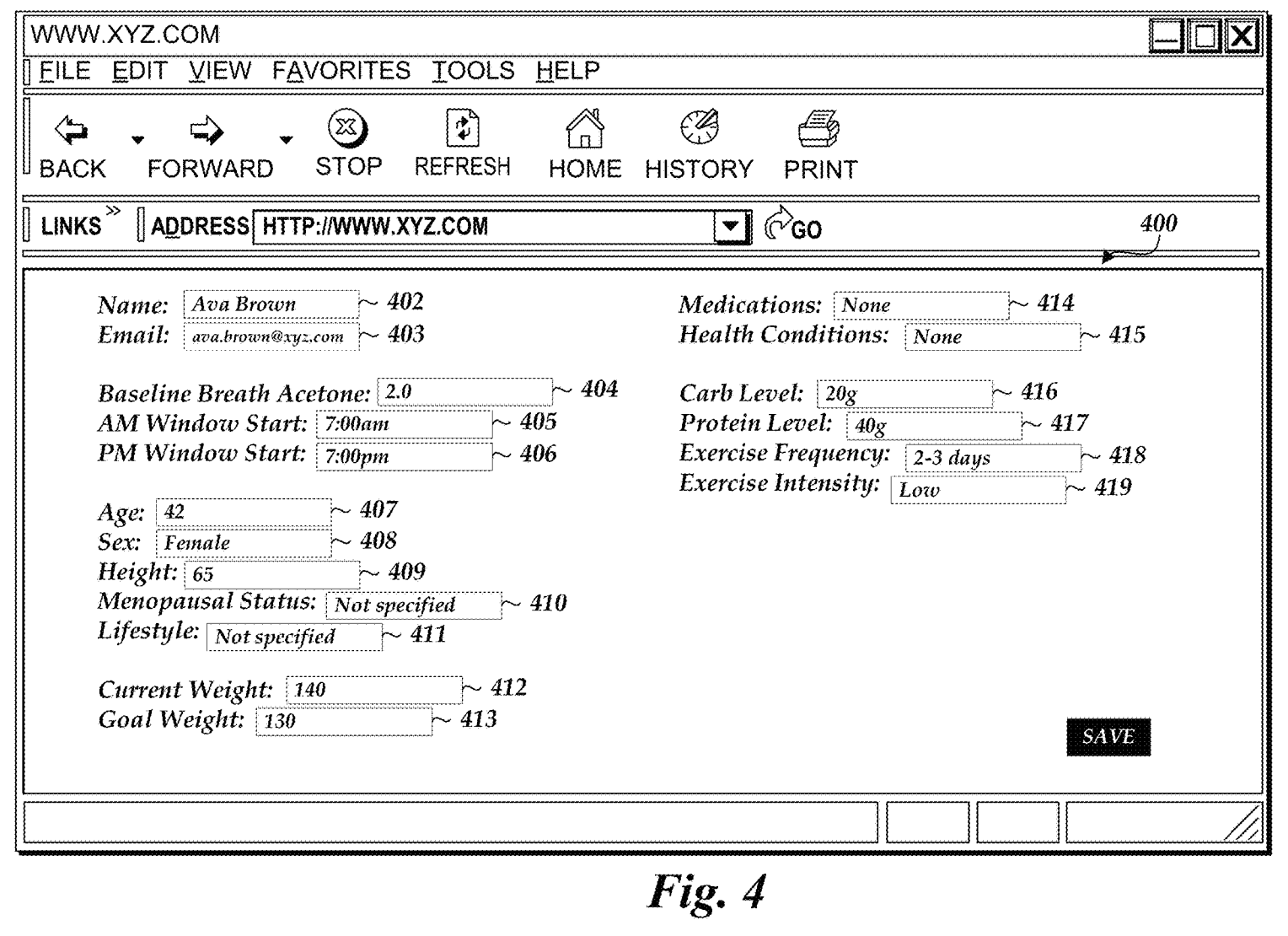

FIG. 4 illustrates a user interface 400 depicting a user profile, according to one embodiment. As an example, the user device 110 may generate the user interface 400 when a user logs in to his or her profile or an agent logs in using login credentials via a web browser or the mobile application 115 (not shown). As illustrated in FIG. 4, the user profile depicted in the user interface 400 includes various fields 402-419. The fields 402-419 may include biographical data of a user associated with the user profile, goals of the user, the medical history of the user, and/or other information.

The data included in the fields 402-419 may be stored in the user database 160. The data may be entered manually by the user or an agent. Alternatively, the fields 402-419 may be auto-populated using data received from an electronic medical records system. The user interface 400 may allow a user or agent to update any of the fields 402-419 and save the changes.

Figure 5A:
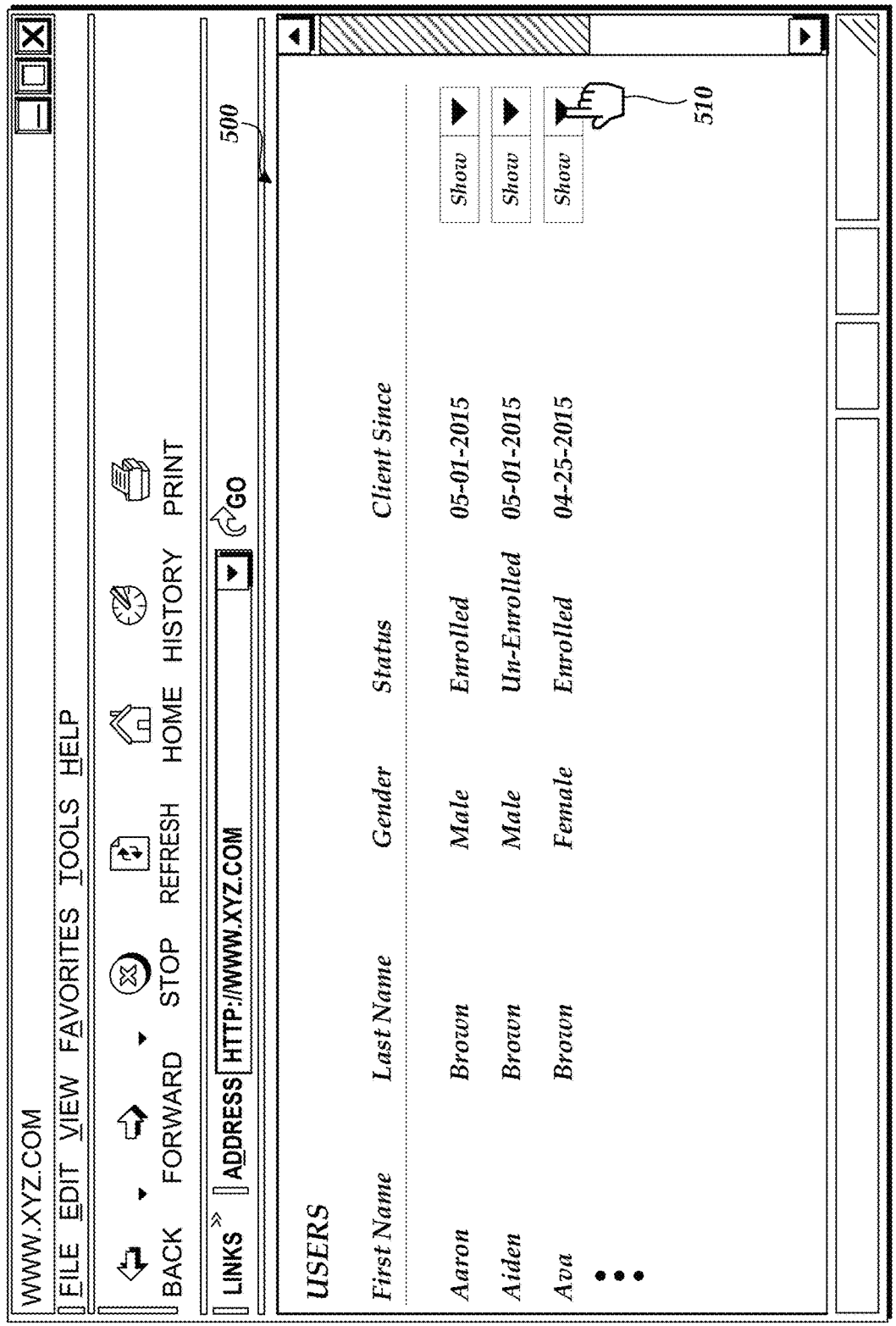
FIGS. 5A-5E illustrate another user interface depicting the assigning of a breath analysis device serial number to a user account, according to one embodiment.

FIGS. 5A-5E illustrate another user interface 500 depicting the assigning of a breath analysis device serial number to a user account, according to one embodiment. As an example, the user device 110 may generate the user interface 500 when a user or agent has logged in via a web browser or the mobile application 115 (not shown). As illustrated in FIG. 5A, the user interface 500 lists users that may wish to run tests using a breath analysis device 130.

Figure 5B:
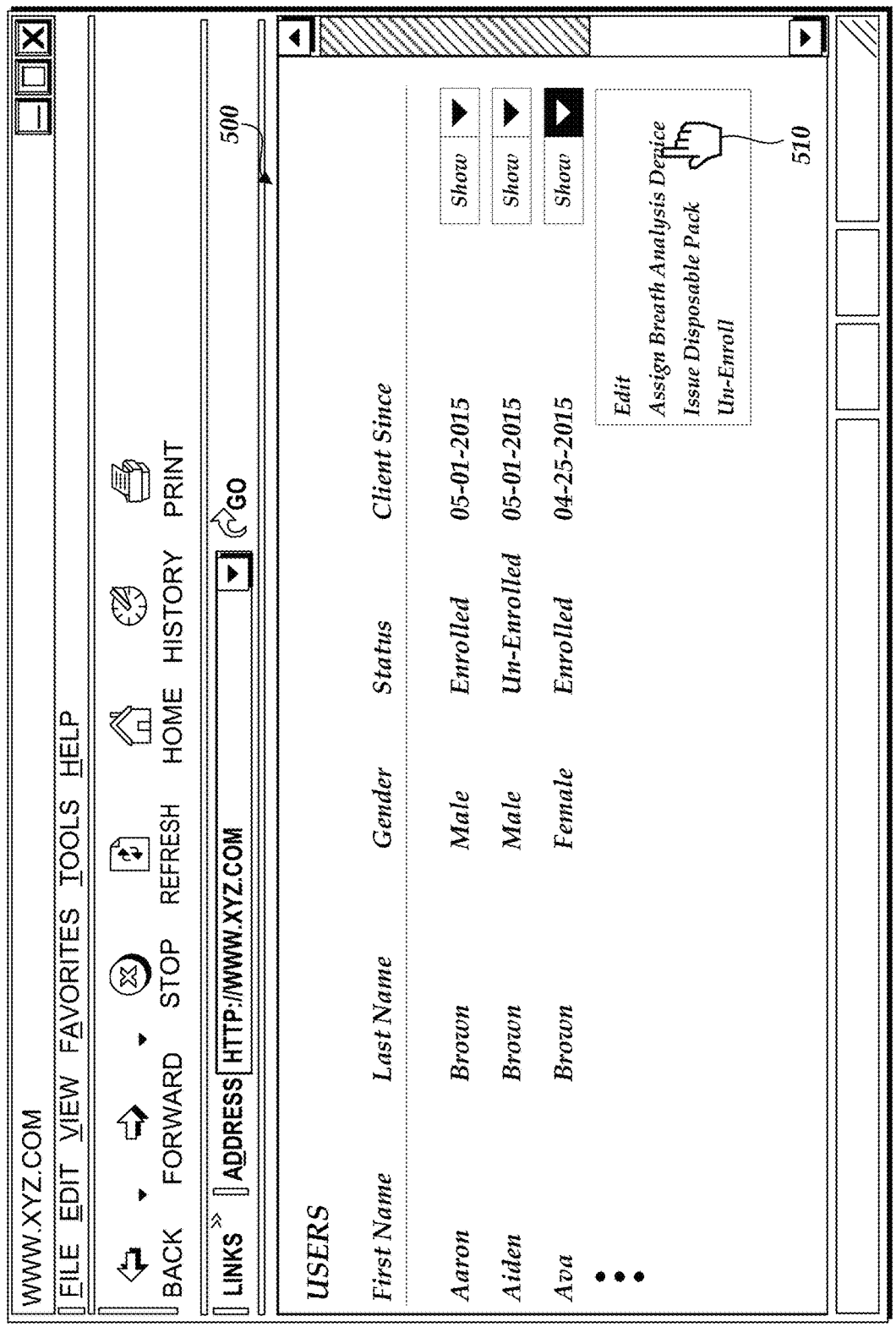

The user or agent may select a show button via cursor 510 to view menu options, as illustrated in FIG. 5B. Menu options include "edit," "assign breath analysis device," "issue disposable pack," and "un-enroll." The "edit" menu option may cause the user interface 500 to display the user profile depicted in FIG. 4 when selected. The "assign breath analysis device" menu option may allow the user or agent to assign a unique identifier (e.g., serial number) to a user, as described below. The "issue disposable pack" may allow the user or agent to assign a specific disposable pack or cartridge to a user, which may be accomplished in a similar manner as described below with the issuance of the unique identifier. The "un-enroll" menu option may allow a user or agent to un-enroll a user from a diet and/or exercise program.

Figure 5C:

As illustrated in FIG. 5B, the user or agent selects the "assign breath analysis device" menu option via cursor 510, which causes the user interface 500 to generate a list of questions as illustrated in FIG. 5C. The user or agent is afforded the opportunity to answer the questions via drop-down buttons 530-538.

Figure 5D:
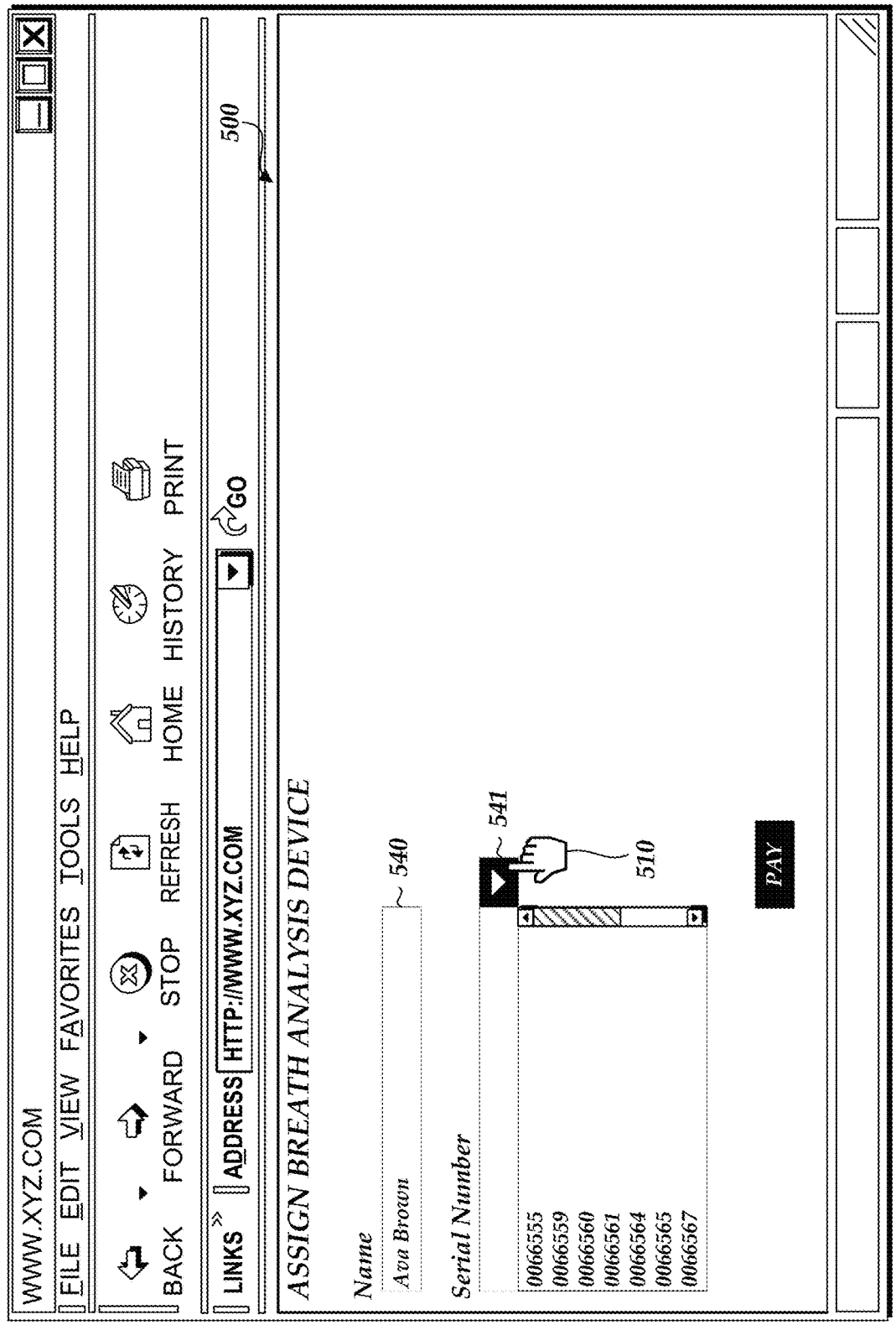

Once the questions are answered, the user or agent may select the save button using cursor 510, which causes the user interface 500 to provide a list of available serial numbers as illustrated in FIG. 5D. The user or agent may select drop-down box 541 via the cursor 510 to view a list of available serial numbers.

Figure 5E:
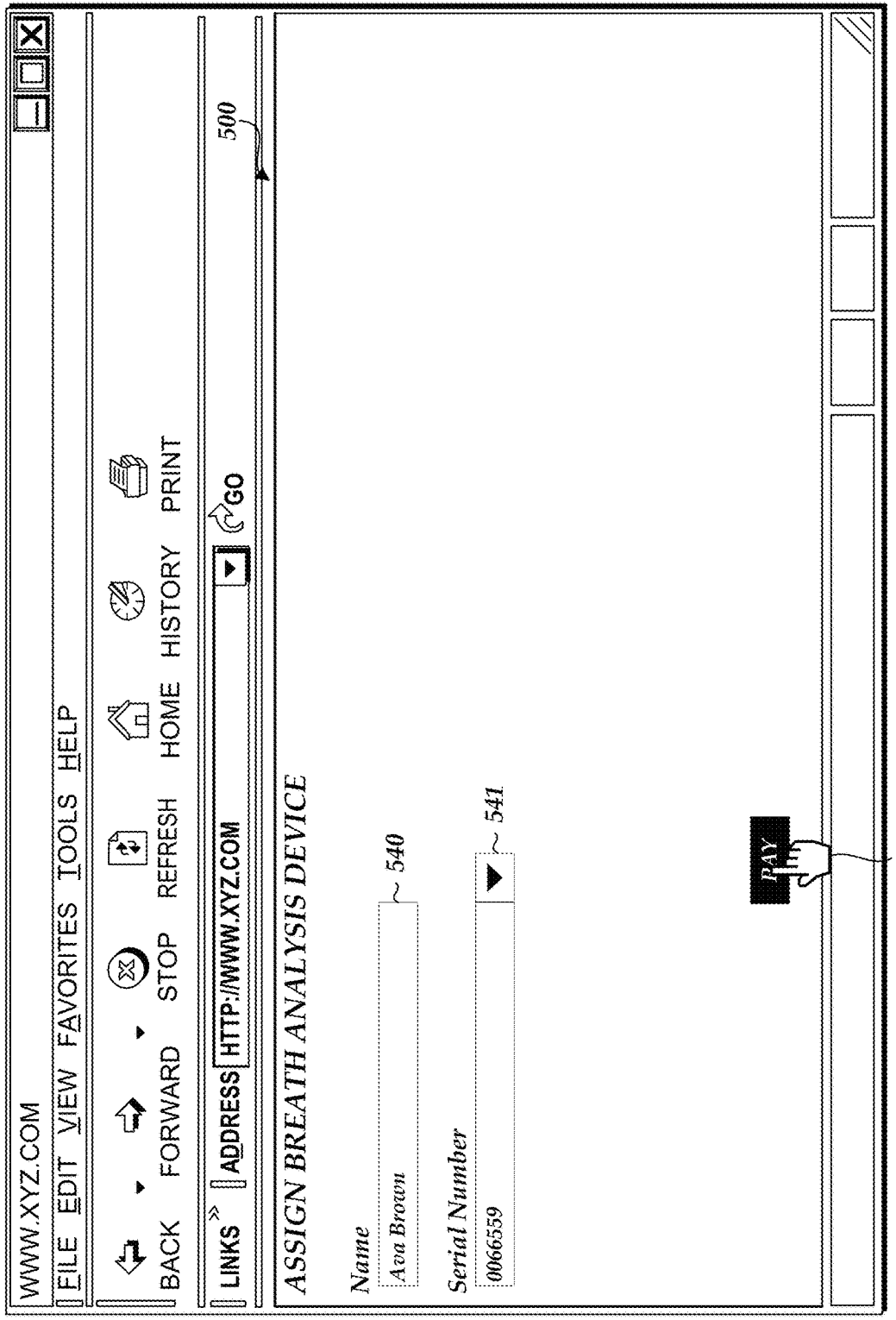

Once a serial number is selected, the user or agent may pay (e.g., acquire the breath analysis device 130 corresponding to the serial number on behalf of the user identified in field 540) by selecting the pay button via the cursor 510 as illustrated in FIG. 5E. Once assigned, the serial number may be displayed when the user profile of the user identified in field 540 is viewed.

Figure 6A:
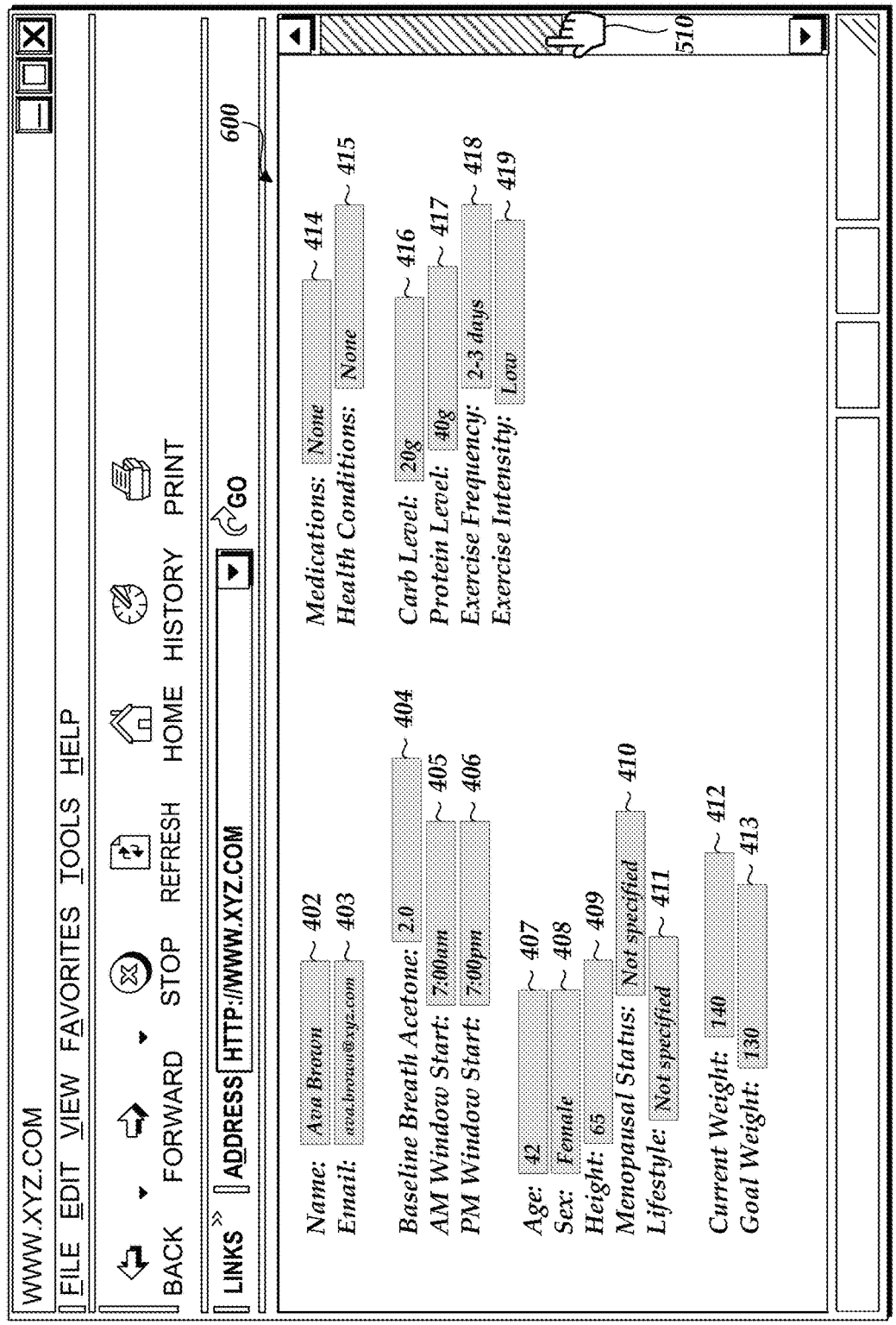
FIGS. 6A-6B illustrate another user interface depicting test results received from a user, according to one embodiment.
Figure 6B:
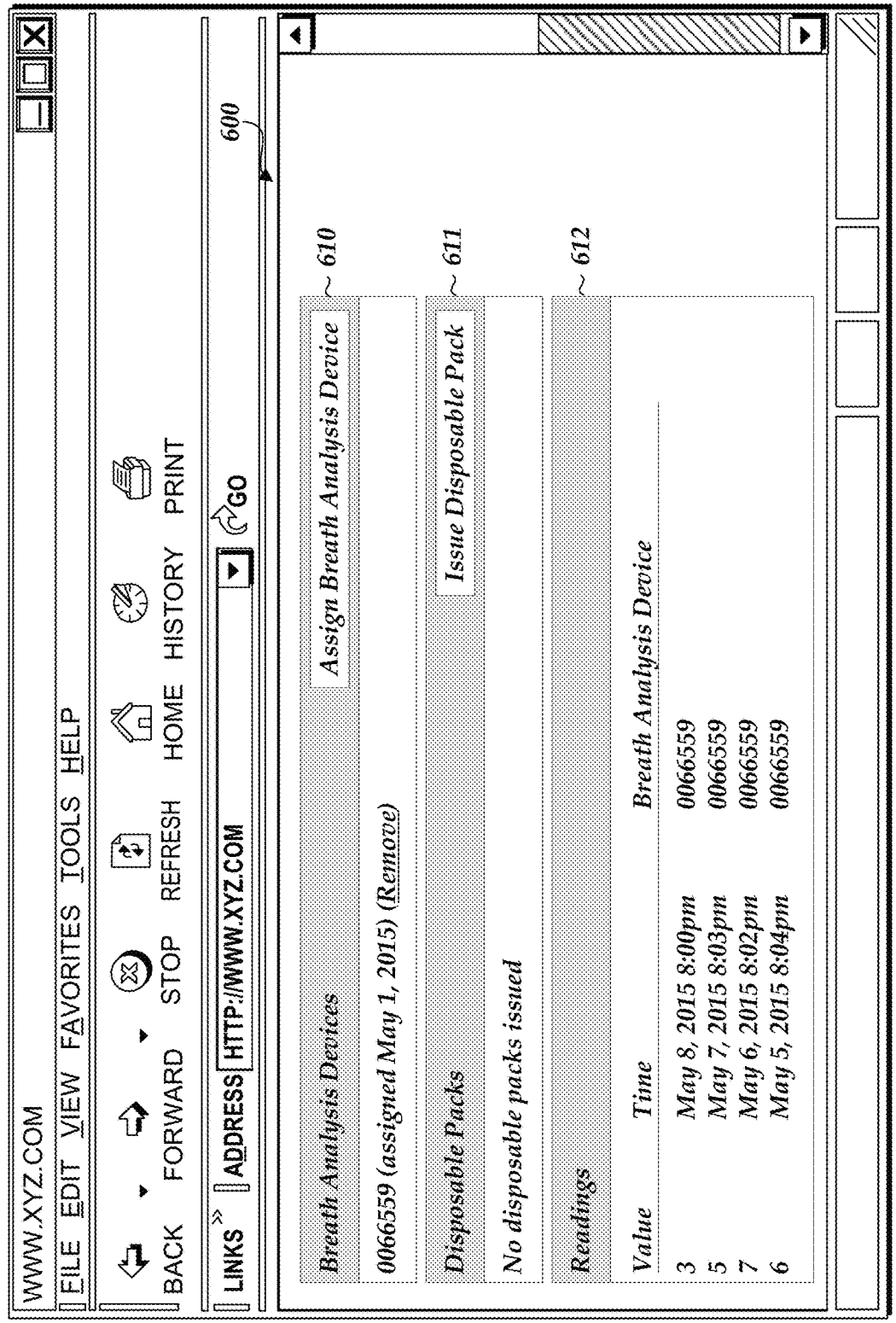

FIGS. 6A-6B illustrate another user interface 600 depicting test results received from a user, according to one embodiment. As an example, the user device 110 may generate the user interface 600 when a user or agent has logged in via a web browser or the mobile application 115 (not shown). As illustrated in FIG. 6A, the user interface 600 displays the user profile depicted earlier in FIG. 4. However, the user profile is not in an editable configuration, as indicated by the grayed-out fields 402-419. Using the cursor 510, the user may scroll down to view additional information.

As illustrated in FIG. 6B, the user profile lists the serial number(s) assigned to the user identified in field 402 in box 610, the serial number(s) of disposable packs assigned to the user identified in field 402 in box 611, and readings or test results for the user identified in field 402 in box 612. The readings may indicate the value parameter received from the breath analysis device 130, the time that the test was completed or the time that the readings were received by the user device 110 and/or server 150, and the serial number of the breath analysis device 130 from which the readings were received.

In an embodiment, the readings are transmitted by the user device 110 (after being received from the breath analysis device 130) to the server 150. The readings may be transmitted automatically without first being displayed to the user via the user device 110 and without allowing the user to block the transmission of the readings to the server 150.

Figure 7:
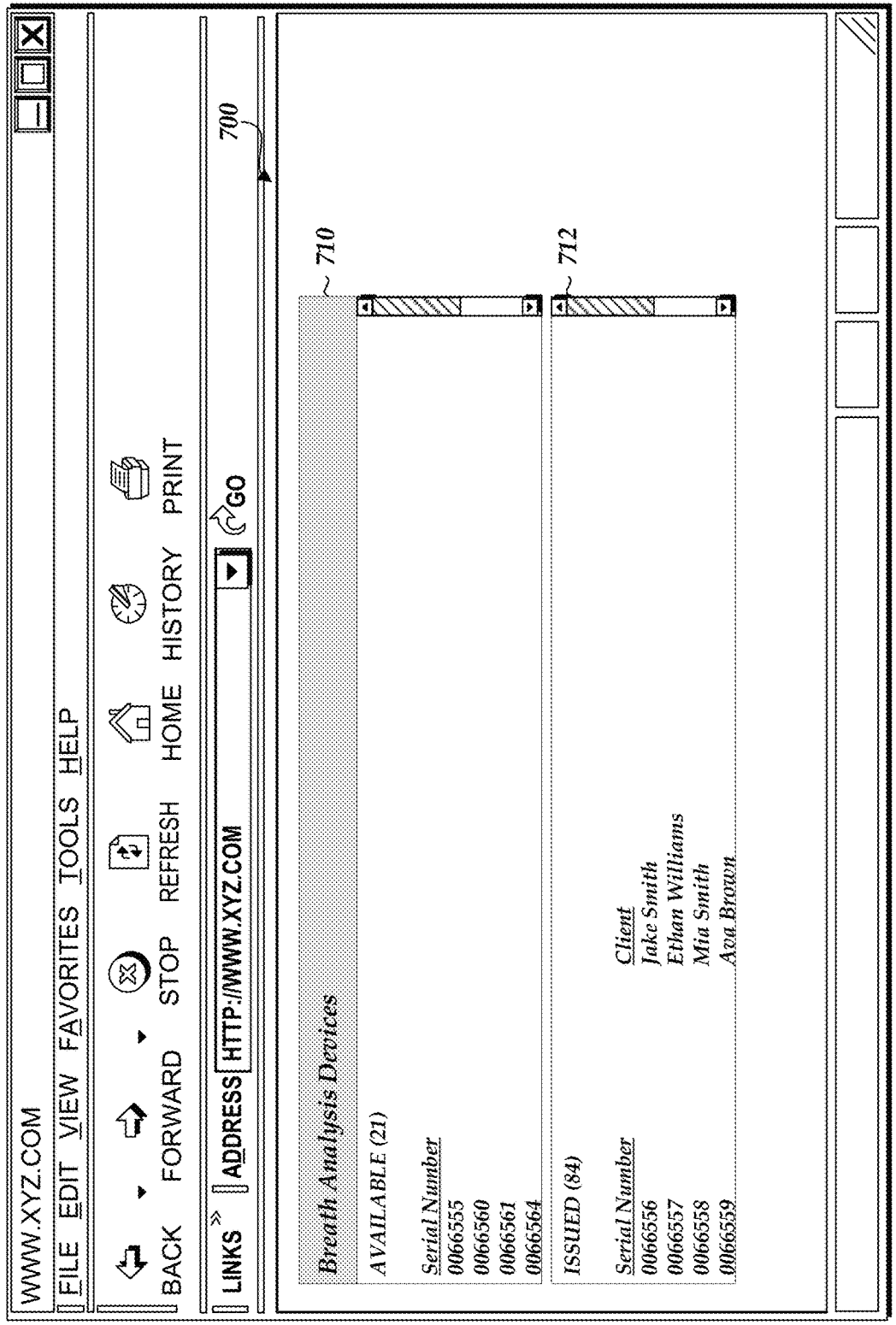
FIG. 7 illustrates another user interface depicting issued and available breath analysis device serial numbers, according to one embodiment.

FIG. 7 illustrates another user interface 700 depicting issued and available breath analysis device serial numbers, according to one embodiment. As an example, the user device 110 may generate the user interface 700 when the mobile application 115 described herein is executed and a user or agent has logged in. As illustrated in FIG. 7, available breath analysis device serial numbers are displayed in box 710 and issued breath analysis device serial numbers are displayed in box 712. A similar user interface may be generated to display available and issued disposable cartridge or pack serial numbers.

Additional Embodiments

The user device 110 can include a wide variety of computing devices, including personal computing devices, terminal computing devices, laptop computing devices, tablet computing devices, electronic reader devices, mobile devices (e.g., mobile phones, media players, handheld gaming devices, etc.), wearable devices with network access and program execution capabilities (e.g., "smart watches" or "smart eyewear"), wireless devices, set-top boxes, gaming consoles, entertainment systems, televisions with network access and program execution capabilities (e.g., "smart TVs"), and various other electronic devices and appliances.

The server 150 can be a computing system configured to provide users and agents (e.g., individuals responsible for coaching users through a diet and/or exercise program) with access to test results. The server 150 may be a single computing device, or it may include multiple distinct computing devices, such as computer servers, logically or physically grouped together to collectively operate as a server system. The components of the server 150 can each be implemented in application-specific hardware (e.g., a server computing device with one or more ASICs) such that no software is necessary, or as a combination of hardware and software. In addition, the modules and components of the server 150 can be combined on one server computing device or separated individually or into groups on several server computing devices. In some embodiments, the server 150 may include additional components not illustrated in FIGS. 1A-1C.

In some embodiments, the features and services provided by the server 150 (e.g., test results) may be implemented as web services consumable via a communication network. In further embodiments, the server 150 is provided by one more virtual machines implemented in a hosted computing environment. The hosted computing environment may include one or more rapidly provisioned and released computing resources, which computing resources may include computing, networking and/or storage devices. A hosted computing environment may also be referred to as a cloud computing environment.

The user device 110 and the server 150 may communicate with each other via one or more communication networks. The network may be a publicly accessible network of linked networks, possibly operated by various distinct parties, such as the Internet. In other embodiments, the network may include a private network, personal area network, local area network, wide area network, cable network, satellite network, cellular telephone network, etc. or combination thereof, each with access to and/or from the Internet.

As described above, in some embodiments, the user database 160 is located external to the server 150. For example, the user database 160 may be stored and managed by a separate system or server and may be in communication with the server 150 via a direct connection or an indirect connection (e.g., via a network). In other embodiments, not shown, the user database 160 is located within the server 150.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users. The tasks described herein as being performed by a particular device (e.g., the user device 110, the breath analysis device 130, etc.) may be embodied in, and performed under the control of, software or firmware executed by, and stored within the memory of, that device.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. To clearly illustrate this interchangeability of hardware and software, various illustrative components, blocks, modules, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A breath analysis system, comprising:
   a first portable breath analysis device that includes a wireless transceiver, the first portable breath analysis device having a first unique identifier;
   a mobile application configured to run on a mobile device of a user and to communicate wirelessly with the first portable breath analysis device; and
   a server system that stores data that associates the first unique identifier of the first portable breath analysis system with authentication information of the user,
   wherein the mobile application comprises executable program code that, when executed, causes the mobile device to at least:
      obtain a second unique identifier from the server system;
      scan for portable breath analysis devices;
      obtain, in response to the scanning, a peripheral identification from the first portable breath analysis device;
      determine whether the first portable breath analysis device was recognized at a previous time using the received peripheral identification;
      in response to a determination that the first portable breath analysis device was not recognized at the previous time,
         obtain the first unique identifier from the first portable breath analysis device,
         compare the first unique identifier with the second unique identifier, and
         pair with the first portable breath analysis device in response to a determination that the first unique identifier and the second unique identifier match.

2. The breath analysis system of claim 1, wherein the mobile device executes the executable program code in response to an input received from the user on the mobile device.

3. The breath analysis system of claim 2, wherein the executable program code, when executed, further causes the mobile device to at least obtain the second unique identifier based on the authentication information of the user.

4. The breath analysis system of claim 2, wherein the executable program code, when executed, further causes the mobile device to authenticate the first portable breath analysis device.

5. The breath analysis system of claim 2, wherein the first portable breath analysis device is further configured to authenticate the mobile device.

6. The breath analysis system of claim 1, wherein the first portable breath analysis device is configured to cause the mobile device to execute the executable program code.

7. The breath analysis system of claim 6, wherein the first portable breath analysis device is further configured to authenticate the mobile device.

8. The breath analysis system of claim 6, wherein the executable program code, when executed, further causes the mobile device to authenticate the first portable breath analysis device.

9. The breath analysis system of claim 6, wherein the first portable breath analysis device is further configured to communicate with the server system to determine that the first portable breath analysis device is authorized to pair with the mobile device.

10. The breath analysis system of claim 9, wherein the first portable breath analysis device is further configured to use the mobile device as a proxy to communicate with the server system.

11. The breath analysis system of claim 10, wherein communications between the first portable breath analysis device and the server system are encrypted using a key not accessible by the mobile device.

12. The breath analysis system of claim 9, wherein the first portable breath analysis device is further configured to use a second mobile device as a proxy to communicate with the server system.

13. The breath analysis system of claim 9, wherein the first portable breath analysis device is further configured to communicate with the server system without use of the mobile device.

14. The breath analysis system of claim 1, wherein the executable program code, when executed, further causes the mobile device to pair with the first portable breath analysis device, in response to a determination that the first unique identifier and the second unique identifier match, using a Bluetooth wireless protocol.

15. A non-transitory computer-readable medium having stored thereon a mobile application configured to run on a mobile device of a user, the mobile application comprising executable program code that directs the mobile device to implement a process, the process comprising:
   receiving a first unique identifier from a server in response to an authentication of user credentials;
   scanning for portable medical measurement devices;
   receiving, in response to the scanning, a peripheral identification from a first portable medical measurement device;
   determining whether the first portable medical measurement device was recognized at a previous time using the received peripheral identification; and in response to a determination that the first portable medical measurement device was not recognized at the previous time,
  obtaining a second unique identifier from the first portable medical measurement device,
  comparing the first unique identifier with the second unique identifier, and
  pairing with the first portable medical measurement device in response to a determination that the first unique identifier and the second unique identifier match.

16. The non-transitory computer-readable medium of claim 15, wherein the process further comprises:
  in response to a determination that the first portable medical measurement device was recognized at the previous time, pairing with the first portable medical measurement device at least partly in response to a determination that the first portable medical measurement device is eligible to pair with the mobile device.

17. The non-transitory computer-readable medium of claim 15, wherein the process further comprises:
  in response to the determination that the first portable medical measurement device was not recognized at the previous time,
    storing in the database an indication that the first portable medical measurement device is not eligible to pair with the mobile device in response to a determination that the first unique identifier and the second unique identifier do not match.

18. The non-transitory computer-readable medium of claim 15, wherein the process further comprises:
  in response to the determination that the first portable medical measurement devices was not recognized at the previous time,
    storing in the database an indication that the first portable medical measurement device is eligible to pair with the mobile device in response to the determination that the first unique identifier and the second unique identifier match.

19. The non-transitory computer-readable medium of claim 15, wherein the first portable medical measurement device comprises a first breath analysis device.

* * * * *